United States Patent
Herr et al.

(10) Patent No.: US 10,088,475 B2
(45) Date of Patent: Oct. 2, 2018

(54) MICROFLUIDIC ASSAY DEVICES AND METHODS FOR MAKING AND USING THE SAME

(71) Applicant: The Regents of the University of California, Oakland, CA (US)

(72) Inventors: Amy E. Herr, Oakland, CA (US); Robert Lin, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 26 days.

(21) Appl. No.: 15/030,232

(22) PCT Filed: Oct. 21, 2014

(86) PCT No.: PCT/US2014/061631
§ 371 (c)(1),
(2) Date: Apr. 18, 2016

(87) PCT Pub. No.: WO2015/061356
PCT Pub. Date: Apr. 30, 2015

(65) Prior Publication Data
US 2016/0238595 A1    Aug. 18, 2016

Related U.S. Application Data

(60) Provisional application No. 61/894,316, filed on Oct. 22, 2013.

(51) Int. Cl.
*B01L 3/00* (2006.01)
*G01N 33/543* (2006.01)
(Continued)

(52) U.S. Cl.
CPC ...... *G01N 33/54366* (2013.01); *B01L 3/5027* (2013.01); *B01L 3/50273* (2013.01);
(Continued)

(58) Field of Classification Search
CPC ......... B01L 2200/12; B01L 2300/0627; B01L 2300/069; B01L 2300/0816;
(Continued)

(56) References Cited

U.S. PATENT DOCUMENTS

| 5,919,712 | A | * | 7/1999 | Herron | C07C 281/02 |
|           |   |   |        |        | 385/12 |
| 2011/0098197 | A1 | * | 4/2011 | Chung | C07K 14/315 |
|           |   |   |        |        | 506/9 |

(Continued)

OTHER PUBLICATIONS

Huges et al. (2012) "Microfluidic Western blotting," PNAS 109(52): 21450-21455.

*Primary Examiner* — Jennifer Wecker
(74) *Attorney, Agent, or Firm* — Rudy J. Ng; Bret Field; Bozicevic, Field & Francis LLP

(57) ABSTRACT

Microfluidic devices for determining whether an analyte is present in a sample are provided. The microfluidic devices include a polymeric medium that includes a first analyte detection domain having a first covalently bound capture member that specifically binds to a first analyte, and a second analyte detection domain having a second covalently bound capture member that specifically binds to a second analyte. Also provided are methods of using the subject microfluidic device, systems and kits that use the subject microfluidic devices, as well as methods of producing the same.

23 Claims, 5 Drawing Sheets

(51) Int. Cl.
*G01N 33/68* (2006.01)
*G01N 33/53* (2006.01)
*G01N 27/447* (2006.01)
*G01N 33/545* (2006.01)
*G01N 33/561* (2006.01)

(52) U.S. Cl.
CPC ... *B01L 3/502707* (2013.01); *B01L 3/502761* (2013.01); *G01N 27/44726* (2013.01); *G01N 27/44791* (2013.01); *G01N 33/545* (2013.01); *G01N 33/54353* (2013.01); *G01N 33/561* (2013.01); *G01N 33/6845* (2013.01); *B01L 2200/12* (2013.01); *B01L 2300/069* (2013.01); *B01L 2300/0627* (2013.01); *B01L 2300/0816* (2013.01); *B01L 2300/12* (2013.01); *B01L 2400/0421* (2013.01)

(58) Field of Classification Search
CPC ........ B01L 2300/12; B01L 2400/0421; B01L 3/5027; B01L 3/502707; B01L 3/50273; B01L 3/502761; G01N 27/44726; G01N 27/44791; G01N 33/54; G01N 33/54366; G01N 33/545; G01N 33/561; G01N 33/6845
See application file for complete search history.

(56) References Cited

U.S. PATENT DOCUMENTS

| | | | |
|---|---|---|---|
| 2011/0177618 A1* | 7/2011 | Herr | B01L 3/502761 436/515 |
| 2012/0142904 A1* | 6/2012 | He | B01D 57/02 530/412 |
| 2012/0329040 A1* | 12/2012 | Herr | B01L 3/5023 435/5 |
| 2013/0156645 A1* | 6/2013 | Hong | G01N 33/545 422/69 |
| 2013/0266956 A1* | 10/2013 | Tia | G01N 33/543 435/7.1 |
| 2014/0148365 A1* | 5/2014 | Schulz | B01L 3/50273 506/39 |
| 2014/0170642 A1* | 6/2014 | Huang | G01N 33/54366 435/5 |
| 2016/0011190 A1 | 1/2016 | Herr et al. | |

* cited by examiner

MICROFLUIDIC ASSAY DEVICES AND METHODS FOR MAKING AND USING THE SAME

CROSS-REFERENCE TO RELATED APPLICATION

Pursuant to 35 U.S.C. § 119 (e), this application claims priority to the filing date of the U.S. Provisional Application No. 61/894,316, filed Oct. 22, 2013, the disclosure of which is herein incorporated by reference.

REFERENCE TO GOVERNMENT SUPPORT

This invention was made with government support under Grant Number 1056035 awarded by the National Science Foundation. The government has certain rights in the invention.

INTRODUCTION

Analyte detection assays, or ligand-binding assays, are biochemical tests that measure the presence or concentration of a macromolecule in a sample. For example, an immunoassay depends on specific recognition between an antigen and an antibody directed against it. In some cases, an analyte, e.g., the antigen of interest, is detected by a reagent that specifically binds to the analyte, e.g., an antibody. In other cases, the scheme is reversed; the analyte is an antibody, and its antigen is used as the binding reagent. For instance, identification of infection by hepatitis C virus (HCV) can be based on detecting anti-HCV immunoglobulin G, using immunoassays, immunoblot assays, and immunochromatography. However, confirmatory diagnostics are presently relegated to centralized laboratories owing to laborious, multi-stage protocols. The capability to perform point-of-care confirmation of infection would positively impact treatment efficacy for infectious diseases such as hepatitis C (HCV) and HIV.

SUMMARY

Microfluidic devices for determining whether an analyte is present in a sample are provided. The microfluidic devices include a polymeric medium that includes a first analyte detection domain having a first covalently bound capture member that specifically binds to a first analyte, and a second analyte detection domain having a second covalently bound capture member that specifically binds to a second analyte. Also provided are methods of using the subject microfluidic device, systems and kits that use the subject microfluidic devices, as well as methods of producing the same.

Aspects of the present disclosure include a microfluidic device that includes a polymeric medium that includes a first analyte detection domain having a first covalently bound capture member that specifically binds to a first analyte, and a second analyte detection domain having a second covalently bound capture member that specifically binds to a second analyte.

In some embodiments, the microfluidic device includes a flow path and a polymeric medium in the flow path. The polymeric medium includes a first analyte detection domain that includes a first covalently bound capture member that specifically binds to a first analyte, and a second analyte detection domain that includes a second covalently bound capture member that specifically binds to a second analyte.

In some embodiments, the first and second covalently bound capture members are different.

In some embodiments, the first and second covalently bound capture members are the same, and the microfluidic device further includes a spacer domain between the first and second analyte detection domains.

In some embodiments, the polymeric medium includes a polyacrylamide gel.

In some embodiments, the first covalently bound capture member is covalently bound to the polymeric medium through a linker group. In some embodiments, the second covalently bound capture member is covalently bound to the polymeric medium through a linker group. In some embodiments, the linker group comprises a benzophenone functional group. In some embodiments, the linker group includes N-(3-[(4-benzoylphenyl)formamido]propyl) methacrylamide. In some embodiments, the linker group includes 3-benzoyl-N-[3-(2-methyl-acryloylamino)-propyl]-benzamide. In some embodiments, the linker group includes a spacer group. In some embodiments, the spacer group includes a $C_1$-$C_6$ alkyl group.

In some embodiments, the first capture member includes an antigen.

In some embodiments, the second capture member includes an antigen.

In some embodiments, the microfluidic device includes two or more polymeric media. Each of the polymeric media includes a first analyte detection domain that includes a first covalently bound capture member that specifically binds to a first analyte, and a second analyte detection domain that includes a second covalently bound capture member that specifically binds to a second analyte.

In some embodiments, the microfluidic device includes two or more flow paths, each of which includes a polymeric medium. The polymeric medium includes a first analyte detection domain that includes a first covalently bound capture member that specifically binds to a first analyte, and a second analyte detection domain that includes a second covalently bound capture member that specifically binds to a second analyte.

Aspects of the present disclosure include a method of determining whether an analyte is present in a sample. The method includes introducing a sample into a microfluidic device that includes a polymeric medium. The polymeric medium includes a first analyte detection domain that includes a first covalently bound capture member that specifically binds to a first analyte, and a second analyte detection domain that includes a second covalently bound capture member that specifically binds to a second analyte. The method also includes applying a directional electric field to the polymeric medium in a manner sufficient to move components in the sample through the polymeric medium, and obtaining a signal from one or more of the first and second analyte detection domains to determine whether the analyte is present in the sample.

In some embodiments, the first capture member includes a first antigen and the first analyte includes a first specific binding member (e.g., a first antibody) that specifically binds to the first antigen. In some embodiments, first specific binding member includes a fluorescent label.

In some embodiments, the second capture member includes a second antigen and the second analyte includes a second specific binding member (e.g., a second antibody) that specifically binds to the second antigen. In some embodiments, the second specific binding member includes a fluorescent label.

In some embodiments, the method further includes introducing a label into the microfluidic device after introducing the sample into the microfluidic device. In some embodiments, the label includes a secondary specific binding member (e.g., a secondary antibody) that specifically binds to the first analyte. In some embodiments, the label includes a secondary specific binding member (e.g., a secondary antibody) that specifically binds to the second analyte. In some embodiments, the label includes a fluorescent moiety.

In some embodiments, the sample includes blood or a blood product.

Aspects of the present disclosure include a system for determining whether an analyte is present in a sample. The system includes a microfluidic device that includes a polymeric medium and a detector. The polymeric medium includes a first analyte detection domain that includes a first covalently bound capture member that specifically binds to a first analyte, and a second analyte detection domain that includes a second covalently bound capture member that specifically binds to a second analyte.

In some embodiments, the system includes a microfluidic device that includes a flow path and a polymeric medium in the flow path, and a detector. The polymeric medium includes a first analyte detection domain that includes a first covalently bound capture member that specifically binds to a first analyte, and a second analyte detection domain that includes a second covalently bound capture member that specifically binds to a second analyte.

In some embodiments, the system further includes one or more microfluidic components configured to direct a fluid through the microfluidic device.

Aspects of the present disclosure include a kit that includes a microfluidic device that includes a polymeric medium and a packaging configured to contain the microfluidic device. The polymeric medium includes a first analyte detection domain that includes a first covalently bound capture member that specifically binds to a first analyte, and a second analyte detection domain that includes a second covalently bound capture member that specifically binds to a second analyte.

In some embodiments, the kit that includes a microfluidic device that includes a flow path and a polymeric medium in the flow path, and a packaging configured to contain the microfluidic device. The polymeric medium includes a first analyte detection domain that includes a first covalently bound capture member that specifically binds to a first analyte, and a second analyte detection domain that includes a second covalently bound capture member that specifically binds to a second analyte.

Aspects of the present disclosure include a method of producing a microfluidic assay device. The method includes producing a polymeric medium that includes functional groups that covalently bond to a capture member upon application of an applied stimulus, introducing into the polymeric medium a first capture member that specifically binds to a first analyte, exposing a first region of the polymeric medium to the applied stimulus to produce a first analyte detection domain that includes the first capture member covalently bound to the polymeric medium, introducing into the polymeric medium a second capture member that specifically binds to a second analyte, and exposing a second region of the polymeric medium to the applied stimulus to produce a second analyte detection domain that includes the second capture member covalently bound to the polymeric medium, to produce the microfluidic assay device.

In some instances, the method includes producing a polymeric medium in a flow path, where the polymeric medium includes functional groups that covalently bond to a capture member upon application of an applied stimulus, introducing into the flow path a first capture member that specifically binds to a first analyte, exposing a first region of the flow path to the applied stimulus to produce a first analyte detection domain that includes the first capture member covalently bound to the polymeric medium, introducing into the flow path a second capture member that specifically binds to a second analyte, and exposing a second region of the flow path to the applied stimulus to produce a second analyte detection domain that includes the second capture member covalently bound to the polymeric medium, to produce the microfluidic assay device.

BRIEF DESCRIPTION OF THE FIGURES

FIG. 1 (panel B) shows a methacrylamide moiety with a benzophenone moiety used as a precursor for a polyacrylamide gel, according to embodiments of the present disclosure. FIG. 1 (panel C) shows a schematic of a covalently bound (immobilized) antigen used as a capture member for a primary antibody in a sample, according to embodiments of the present disclosure. The captured primary antibody may be labeled using a secondary antibody.

FIG. 2 (panel B) shows an electropherogram of each of the three patterning cycles.

FIG. 3 (panel B) shows corresponding electropherograms of the experiment shown in FIG. 3 (panel A). FIG. 3 (panel C) shows a comparison between equivalent regions of interest (ROIs) at the patterned BSA band and off-target protein band as shown at the bottom of FIG. 3 (panel A). The inset in FIG. 3 (panel C) shows a graph of the signal-to-noise ratio (SNR) over the loading period.

FIG. 4 (panel A) shows a schematic of pattern used to test antibody capture. AF488-OVA and UV were negative control bands. Unlabelled BSA was the targeted antigen. FIG. 4 (panel B) shows electropherogram and fluorescence images of the microchannel after photopatterning. Only AF488-OVA was detected. FIG. 4 (panel C) shows images after primary antibody probing and washout. A signal was detected at the location of photopatterned BSA. FIG. 4 (panel D) shows images after secondary blotting and washout. A clear signal appeared at the location of photopatterned BSA. The dotted line represents the averaged signal from 3 channels and green (shaded area) represents 1 S.D. above and below the mean.

FIG. 5 (panel B) shows a fluorescence image taken after patterning of all five bands. FIG. 5 (panel C) shows results from four simultaneous assays performed on four different human serum samples.

DETAILED DESCRIPTION

Figure 1:
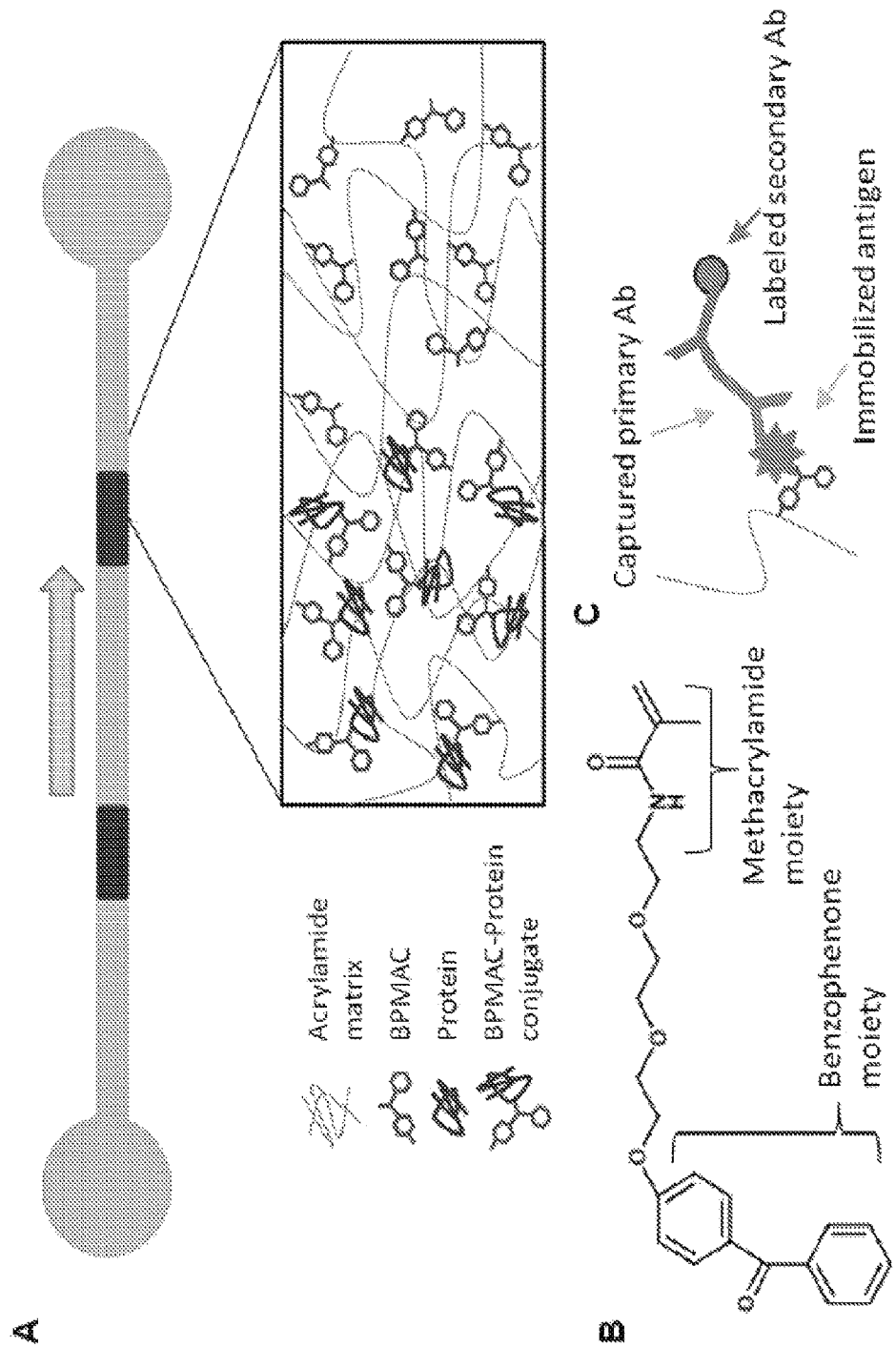
FIG. 1 (panel A) shows a schematic of a photopatterned barcode device, according to embodiments of the present disclosure.

Microfluidic devices for determining whether an analyte is present in a sample are provided. The microfluidic devices include a polymeric medium that includes a first analyte detection domain having a first covalently bound capture member that specifically binds to a first analyte, and a second analyte detection domain having a second covalently bound capture member that specifically binds to a second analyte. Also provided are methods of using the subject microfluidic device, systems and kits that use the subject microfluidic devices, as well as methods of producing the same.

Below, the subject microfluidic devices are described first in greater detail. Methods of detecting an analyte in a fluid sample are also disclosed in which the subject microfluidic devices find use. In addition, systems and kits that include the subject microfluidic devices are also described.

Microfluidic Devices

Embodiments of the present disclosure include microfluidic devices. A "microfluidic device" is a device that is configured to control and manipulate fluids geometrically constrained to a small scale (e.g., sub-millimeter). Embodiments of the microfluidic devices include a flow path and a polymeric medium. The polymeric medium is disposed in at least a portion of the flow path of the microfluidic device. For example, the polymeric medium may be present in substantially the entire length of the flow path of the microfluidic device. In certain embodiments, the polymeric medium includes a covalently bound capture member that specifically binds to an analyte of interest in a sample. The capture member may specifically bind to an analyte in a sample as the sample traverses through the flow path of the microfluidic device. The specifically bound analyte may then be detected.

In some instances, the polymeric medium is defined by a region of the microfluidic device that includes the polymeric medium. For example, as indicated above, the microfluidic device may include a flow path in which the polymeric medium is present. In some cases, the flow path is an elongated flow path. The elongated flow path may include the polymeric medium as described above. For instance, the microfluidic device may include an elongated flow path, where the elongated flow path is a channel (e.g., a microfluidic channel). The channel may include the polymeric medium. The polymeric medium may be included in the channel, such that a sample to be analyzed for the presence of an analyte traverses the polymeric medium as the sample flows through the channel. In some instances, the length of the elongated flow path is greater than the width of the elongated flow path, such as 2 times, 3 times, 4 times, 5 times, 10 times, 25 times, 50 times, 75 times, 100 times, 125 times, 150 times, 175 times, or 200 or more times greater than the width of the elongated flow path.

Polymeric Medium

In certain embodiments, the microfluidic device includes a polymeric medium. The polymeric medium may be present in the flow path of the microfluidic device as described above. In some cases, the polymeric medium is a contiguous polymeric medium present in the flow path of the microfluidic device. In certain embodiments, the polymeric medium is configured to bind to one or more constituents in a sample as the sample traverses the polymeric medium. For instance, the polymeric medium may include a capture member. In some cases, a capture member of the polymeric medium is configured to specifically bind to a constituent in the sample (e.g., an analyte of interest) as the sample flows through the polymeric medium.

The capture member may be present in one or more regions of the polymeric medium, such as in 1 or more, or 2 or more, or 3 or more, or 4 or more, or 5 or more, or 6 or more, or 7 or more, or 8 or more, or 9 or more, or 10 or more distinct regions of the polymeric medium. In some instances, a region of the polymeric medium that includes the capture member is referred to as an "analyte detection domain" or a "band". By "analyte detection domain" or "band" is meant a distinct detectable region of the polymeric medium where a capture member is localized (e.g., covalently bound to the polymeric medium). In some instances, the polymeric medium may be configured to have two or more separate analyte detection domains or bands for the capture members. Each analyte detection domain may include a single type of capture member. In some cases, different distinct analyte detection domains may include the same capture member, such that the analyte detection domains specifically bind to the same analyte in the sample. For example, the polymeric medium may include a first analyte detection domain and a second analyte detection domain, where the first and second analyte detection domains include a capture member that specifically binds to an analyte. In some cases, different distinct analyte detection domains may include different capture members, such that distinct analyte detection domains specifically bind to different analytes of interest in the sample. As indicated above, multiple analyte detection domains may be present in a single flow path (e.g., in a single polymeric medium). Thus, multiple different analytes, each specifically bound by a distinct analyte detection domain, may be detected in a single flow path (e.g., in a single polymeric medium). For example, the polymeric medium may include a first analyte detection domain having a first capture member that specifically binds to a first analyte, and a second analyte detection domain having a second capture member that specifically binds to a second analyte. Additional capture members present in additional analyte detection domains may be included as desired.

In certain embodiments, an analyte detection domain has a length that is less than the overall length of the polymeric medium. In some instances, an analyte detection domain has a length ranging from 10 μm to 1000 μm, such as 10 μm to 900 μm, or 10 μm to 800 μm, or 10 μm to 700 μm, or 10 μm to 600 μm, to 10 μm to 500 μm, or 10 μm to 400 μm, or 10 μm to 300 μm, or 10 μm to 200 μm, or 10 μm to 100 μm, or 25 μm to 100 μm, or 50 μm to 100 μm. In some embodiments, the analyte detection domain has a length of 100 μm. The width and depth of the analyte detection domain may be the same as the width and depth of the polymeric medium and/or microfluidic channel, as described in more detail below.

In certain embodiments, the polymeric medium includes one or more spacer domains. The spacer domain may be a region of the polymeric medium that does not include a significant amount of a capture member. For instance, a spacer domain may include substantially no capture members. In some cases, the spacer domain does not include a capture member that is covalently bound to the polymeric medium. The spacer domain may be present in the polymeric medium adjacent to an analyte detection domain. For example, the spacer domain may be adjacent to an analyte detection domain or may be present between two analyte detection domains. The spacer domain may be in fluid communication with the adjacent analyte detection domains.

In some cases, the spacer domain(s) and analyte detection domain(s) are present in a contiguous polymeric medium. For instance, the polymeric medium may include a first analyte detection domain and a second analyte detection domain, where the first and second analyte detection domains include a capture member that specifically binds to an analyte, and a spacer domain between the first and second analyte detection domains. In other embodiments, the polymeric medium includes a first analyte detection domain having a first capture member that specifically binds to a first analyte, a second analyte detection domain having a second capture member that specifically binds to a second analyte, and a spacer domain between the first and second analyte detection domains.

The polymeric medium may include one or more control regions, such as a negative control region and/or a positive control region. For instance, a negative control region may be a region of the polymeric medium that does not include a capture member or that includes a moiety (e.g., an antigen) that is not specifically bound by the analyte of interest in the sample. In some instances, a negative control region may facilitate detection of the cross-reactivity of an analyte in a sample with off-target moieties (e.g., non-specific binding of an analyte in a sample to a negative control moiety). In some cases, the polymeric medium includes a positive control region, where the positive control region includes a moiety (e.g., an antigen) that binds to multiple different analytes in the sample. For example, a positive control region may include a capture member that binds to a wide range of analytes in the sample, such as a capture member that is not specific for only one analyte but binds to several different analytes in the sample. An example of a capture member that binds to several analytes is Protein L, which binds to antibodies of several different antibody classes, including IgG, IgM, IgA, IgE and IgD. In some cases, a positive control region may facilitate detection of sufficient sample loading on the polymeric medium.

In certain embodiments, the capture member is covalently bound to the polymeric medium. Stated another way, the polymeric medium may include a covalently bound capture member, e.g., a capture member that includes one or more covalent bounds to the polymeric medium. In some instances, the capture member is covalently bound to a support (e.g., the polymeric medium), such as cross-linked or copolymerized to the support. Covalent bonds between the capture member and the support include covalent bonds that involve reactive groups, such as, but not limited to, the following: glutaraldehyde, which utilizes the bifunctional linker glutaraldehyde to form covalent bonds with the amino/amide groups of both the capture member and the support; glycidyl methacrylate, which utilizes the glycidyl functional group (i.e., the epoxy functional group) for covalent bonding to the capture member and a methacrylate group for binding to the support; 4-nitrophenyl methacrylate, which can be used to acylate amine groups of the capture member to covalently bind to the support; N-hydroxysuccinimidyl acrylate (NHS-acrylate), which utilizes the N-hydroxysuccinimidyl group to interact with amino groups on the capture member for incorporation into the support. For example, the polymeric medium may include a first analyte detection domain having a first covalently bound capture member that specifically binds to a first analyte, and a second analyte detection domain having a second covalently bound capture member that specifically binds to a second analyte.

In certain embodiments, the support (e.g., the polymeric medium) includes a covalently bound capture member, where during fabrication of the polymeric medium, the covalent bond between the polymeric medium and the capture member is formed upon application of an applied stimulus. For example, the applied stimulus may include electromagnetic radiation, such as light. In some cases, the light is ultraviolet (UV) light. In some instances, the light used to covalently bond the capture member to the polymeric medium has a wavelength ranging from 10 nm to 400 nm, such as from 50 nm to 400 nm, including from 100 nm to 400 nm, or from 150 nm to 400 nm, or from 200 nm to 400 nm, or from 250 nm to 400 nm, or from 300 nm to 400 nm, or form 325 nm to 375 nm, or from 350 nm to 365 nm. In certain cases, the light has a wavelength ranging from 350 to 365 nm.

In some cases, the polymeric medium includes functional groups that covalently bond to the capture member during fabrication of the polymeric medium. For example, the capture member may be a protein, a peptide, such as an antigen, an antibody or fragment thereof, and the like. The functional groups on the polymeric medium may include functional groups that are activated upon application of an applied stimulus, such as electromagnetic radiation (e.g., light) as described above. As such, in certain instances, the functional groups are light-activatable functional groups. Upon application with light, the light-activatable functional groups may form a reactive species capable of forming covalent bonds, such as a radical alkyl intermediate, with the capture member. Examples of functional groups that may covalently bond to the capture member upon application of an applied stimulus (e.g., light) include, but are not limited to, benzophenone groups, and the like. Once activated by the applied stimulus, the functional group may bond to the capture member, thus forming a covalent bond between the polymeric medium and the capture member. For example, the functional group may form a carbon-carbon bond between the functional group and the capture member, thus covalently bonding the capture member to the polymeric medium.

In some embodiments, the functional groups are co-polymerized with the polymeric medium. The functional groups may be co-polymerized with the polymeric medium during the production process for the polymeric medium. For example, the functional groups may include a linker group that is attached to the polymeric medium. Stated another way, the capture member may be covalently bound to the polymeric medium through a linker group. The linker group may include a functional group, which forms a covalent bond to the capture member as described above. The functional group may be attached to the linker group at a first end of the linker group, and a second end of the linker group may be bound to the polymeric medium, thereby indirectly bonding the functional group to the polymeric medium. In some instances, the second end of the linker group, which is bound to the polymeric medium, includes a co-monomer, such as, but not limited to, an acrylamide co-monomer, and the like. In some embodiments, the second end of the linker group includes a methacrylamide co-monomer. In certain cases, the functional group (e.g., the functional group at the first end of the linker group) is a benzophenone functional group and the linker group includes a co-monomer (e.g., at the second end of the linker group), such as an acrylamide co-monomer. For example, the linker group (e.g., including the functional group and the co-monomer) may be N-(3-[(4-benzoylphenyl)formamido] propyl) methacrylamide (also known as BPMA or BPMAC) or 3-benzoyl-N-[3-(2-methyl-acryloylamino)-propyl]-benzamide (BP-APMA); the structures of each of which are shown below. As described above, the linker group may have the functional group attached at a first end, and the second end of the linker group bound to the polymeric medium. In some instances, the linker group includes a spacer group, such as a spacer group between the first end and the second end of the linker group (e.g., a spacer group in the middle portion of the linker group between the functional group and the co-monomer). In some cases, the spacer group of the linker group between the first and second ends of the linker group includes an aliphatic group, such as, but not limited to, a $C_{1-10}$ alkyl group. In certain cases, the spacer group of the linker group includes a lower alkyl group (e.g., a $C_{1-6}$ alkyl group, or a $C_{1-5}$ alkyl group, or a $C_{1-4}$ alkyl group, or a $C_{1-3}$ alkyl group, or a $C_{1-2}$ alkyl group). For instance, the spacer group of the linker group may include a propyl group.

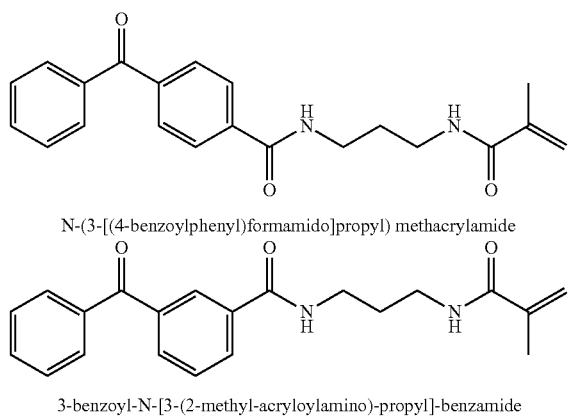

N-(3-[(4-benzoylphenyl)formamido]propyl) methacrylamide 3-benzoyl-N-[3-(2-methyl-acryloylamino)-propyl]-benzamide A capture member can be any molecule that specifically binds to another binding member of interest, e.g., a protein or nucleic acid sequence or biomacromolecule that is being targeted (e.g., the analyte of interest). Specific binding between a capture member and its specific binding partner can form a stable association between the capture member and its binding partner. By "stable association" is meant that a moiety is bound to or otherwise associated with another moiety or structure under standard conditions. In certain instances, the stable associate creates a bond between the capture member and its specific binding partner, which bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. In some embodiments, the affinity between a capture member and its specific binding partner in a binding complex is characterized by a $K_D$ (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding; increased binding affinity being correlated with a lower $K_D$.

Depending on the nature of the analyte, capture members can be, but are not limited to, (a) antigens for the detection of specific anti-antigen antibodies; (b) antibodies against an epitope of the peptidic analyte for the detection of proteins and peptides; (c) any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like.

In certain embodiments, the capture member includes an antigen. The capture member antigen may specifically bind to an analyte of interest in a sample, such as an antibody of interest in the sample or a fragment thereof. In certain embodiments, the capture member includes an antibody. In certain embodiments, the capture member includes an antibody fragment. The capture member antibody may specifically bind to an analyte of interest in a sample, such as an antigen of interest in the sample. In some cases, the capture member is covalently bound to a support (e.g., the polymeric medium), as described above. The support-bound capture member may be configured to specifically bind to the analyte of interest. As such, specific binding of the analyte of interest to the support-bound capture member may indirectly bind the analyte of interest to the support. Binding of the analyte of interest to the support may stably associate the analyte with the support and thus facilitate detection of the analyte of interest.

In certain embodiments, two or more different capture members are stably associated with the polymeric medium to provide distinct detection regions that include different capture members. The two or more different capture members may specifically bind to the same or different analytes. In some cases, the two or more different capture members may specifically bind to different analytes. For example, the two or more capture members may include different antigens that specifically bind to different antibodies (or fragments thereof) in the sample. In other cases, the two or more different capture members may specifically bind to the same analyte. For instance, two or more different capture member antigens may be used to detect cross-reactivity of an antibody to different antigens.

In certain embodiments, the polymeric medium includes a polymer, such as a polymeric gel. The polymeric gel may be a gel suitable for gel electrophoresis. The polymeric gel may include, but is not limited to, a polyacrylamide gel (e.g., methacrylamide gel), an agarose gel, and the like. The polymeric medium may be characterized based on various factors, such as, but not limited to, pore size, total polymer content (e.g., total acrylamide content), concentration of cross-linker, and the like. For instance, the polymeric medium may have a pore size that depends on the total polymer content of the polymeric medium and/or the concentration of cross-linker in the polymeric medium. In some cases, the polymeric medium may include a polyacrylamide gel that has a total acrylamide content, T (T=total concentration of acrylamide and bisacrylamide monomer), ranging from 1% to 20%, such as from 2% to 15%, including from 2% to 10%. In some instances, the polymeric medium has a total acrylamide content of 4%.

In certain embodiments, the polymeric medium is configured to be formed from precursor moieties. For example, the polymeric medium may be a gel (e.g., a polyacrylamide gel) formed form gel precursors (e.g., polyacrylamide gel precursors, such as polyacrylamide monomers). The precursor moieties may be configured to react to form the polymeric medium. For instance, the gel precursors may be configured to react with each other to form the polyacrylamide gel polymeric medium. The reaction between the gel precursors may be activated by any suitable protocol, such as, but not limited to, chemical activation, light activation, etc. In some embodiments, the gel precursors are configured to be activated chemically, for example by contacting the gel precursors with an activation agent, such as, but not limited to, a peroxide. In some embodiments, the gel precursors are configured to be activated by light (i.e., photo-activated), for instance by contacting the gel precursors with light. The light may be of any wavelength suitable for activating the formation of the polymeric medium, and in some instances may have a wavelength associated with blue light in the visible spectrum. In some instances, the light used to activate polymerization of the polymeric medium is of a different wavelength than the light used to activate the functional groups used to covalently bond the capture members to the polymeric medium. For example, the light used to activate formation of the polymeric medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the polymeric medium has a wavelength ranging from 465 to 475 nm. In some instances, the light used to activate formation of the polymeric medium has a wavelength of 470 nm.

In certain embodiments, the polymeric medium includes a buffer. The buffer may be any convenient buffer used for gel electrophoresis. In certain embodiments, the buffer is a Tris buffer. In certain embodiments, the polymeric medium includes a buffer, such as a Tris-glycine buffer (TG buffer). For example, the buffer may include a mixture of Tris and glycine.

Aspects of the polymeric medium include that the polymeric medium has a directional axis. In some instances, the directional axis is oriented in the direction the sample travels as the sample traverses the polymeric medium. In some embodiments, the directional axis of the polymeric medium is aligned with the length of the polymeric medium. In these embodiments, the sample traverses the polymeric medium along the length of the polymeric medium. In some cases, the length of the polymeric medium is greater than the width of the polymeric medium, such as 2 times, 3 times, 4 times, 5 times, 10 times, 25 times, 50 times, 75 times, 100 times, 125 times, 150 times, 175 times, or 200 times or more the width of the polymeric medium.

In certain embodiments, the microfluidic device is configured to direct the sample through the polymeric medium. In some instances, the microfluidic device is configured to subject a sample to a flow field. By "flow field" is meant a region where moieties traverse the region in substantially the same direction. For example, a flow field may include a region where mobile moieties move through a medium in substantially the same direction. A flow field may include a medium, such as a polymeric medium, where moieties, such as buffers, analytes, reagents, etc., move through the medium in substantially the same direction. A flow field may be induced by an applied electric field, a pressure differential, electroosmosis, and the like. In some embodiments, the flow field is directional. For example, a flow field may be aligned with the directional axis of the flow path of the polymeric medium. The flow field may be configured to direct the sample or analytes through the polymeric medium along the flow path of the polymeric medium.

The electric fields may facilitate the movement of the sample through the microfluidic device (e.g., electrokinetic transfer of the sample from one end of the microfluidic device to another end of the microfluidic device). For instance, the electric field may be configured to direct the analytes in a sample through the polymeric medium of the microfluidic device. The electric field may be configured to facilitate the movement of the analytes in a sample based on the physical properties of the analytes. For example, the electric field may be configured to facilitate the movement of the analytes in the sample based on the charge (e.g., charge to mass ratio), isoelectric point, etc. of the analytes. In certain instances, the electric field is configured to facilitate the movement of the analytes in the sample based on the charge of the analytes. In some cases, the electric field is configured to facilitate the movement of the analytes in the sample based on the isoelectric point of the analytes.

In some embodiments, the electric field may be directional. For example, an electric field may be aligned with the directional axis of the flow path of the polymeric medium. The electric field may be configured to direct the sample or analytes through the polymeric medium along the flow path of the polymeric medium.

In certain embodiments, the microfluidic device includes one or more electric field generators configured to generate an electric field. The electric field generator may be configured to apply an electric field to various regions of the microfluidic device, such as the polymeric medium. The electric field generator may be configured to electrokinetically transport the analytes and moieties in a sample through the polymeric medium in the microfluidic device. In certain instances, the electric field generator may be proximal to the microfluidic device, such as arranged on the microfluidic device. In some cases, the electric field generator is positioned a distance from the microfluidic device. For example, the electric field generator may be incorporated into a system for detecting an analyte, as described in more detail below.

The microfluidic device may include one or more channels. As described above, the polymeric medium may be present in the channel. In some instances, the channel is a microfluidic channel. A microfluidic channel may have one or more dimensions (e.g., width and/or depth) in the micrometer range (e.g., ranging from 1 µm to 1000 µm). Embodiments of the microfluidic channels may be made of any suitable material that is compatible with the microfluidic devices and compatible with the polymeric medium, capture members, samples, buffers, reagents, etc. used in the microfluidic devices. In some cases, the microfluidic channels are made of a material that is inert (e.g., does not degrade or react) with respect to the polymeric medium, capture members, samples, buffers, reagents, etc. used in the subject microfluidic devices and methods. For instance, the microfluidic channels may be made of materials, such as, but not limited to, glass, quartz, polymers, elastomers, paper, combinations thereof, and the like.

In certain embodiments, the microfluidic channels have a length ranging from 0.5 mm to 5 mm, such as from 0.5 mm to 3 mm, including from 1 mm to 2 mm. In certain instances, the microfluidic channel has a length of 1.2 mm. In certain embodiments, the microfluidic channels have a width ranging from 1 µm to 500 µm, such as from 5 µm to 300 µm, including from 10 µm to 200 µm, for example from 50 µm to 150 µm. In some cases, the microfluidic channel has a width of 90 µm. In certain embodiments, the microfluidic channels have a depth ranging from 1 µm to 200 µm, such as from 5 µm to 100 µm, including from 10 µm to 50 µm. In some cases, the microfluidic channels have a depth of 20 µm.

In some instances, the microfluidic device includes one or more sample input reservoirs. The sample input reservoir may be configured to allow a sample to be introduced into the microfluidic device. The sample input reservoir may be in fluid communication with the polymeric medium (e.g., in fluid communication with the microfluidic channel containing the polymeric medium). In some instances, the sample input reservoir is in fluid communication with the upstream end of the polymeric medium. The sample input reservoir may further include a structure configured to prevent fluid from exiting the sample input reservoir. For example, the sample input reservoir may include a cap, valve, seal, etc. that may be, for instance, punctured or opened to allow the introduction of a sample into the microfluidic device, and then re-sealed or closed to substantially prevent fluid, including the sample and/or buffer, from exiting the sample input reservoir. In certain embodiments, the sample input reservoir is in the shape of a cylindrical well. Other shapes are also possible, such as, but not limited to, a square-shaped well, a rectangular-shaped well, and the like. In some instances, the sample input reservoir has a diameter ranging from 0.5 mm to 5 mm, such as 1 mm to 5 mm, or 1 mm to 4 mm, or 1 mm to 3 mm. In some instances, the sample input reservoir has a diameter of 2 mm. In some instances, the sample input reservoir has a depth ranging from 0.1 mm to 5 mm, such as 0.5 mm to 5 mm, or 0.5 mm to 4 mm, or 0.5 mm to 3 mm, or 0.5 mm to 2 mm. In some instances, the sample input reservoir has a depth of 1 mm.

In certain embodiments, the polymeric gel has a width ranging from 0.1 μm to 500 μm, such as from 0.2 μm to 250 μm, including from 0.5 μm to 150 μm, or 1 μm to 100 μm, or 10 μm to 100 μm, or 25 μm to 100 μm, or 50 μm to 100 μm. In some cases, the polymeric gel has a width of 90 μm. In some instances, the polymeric gel has a length ranging from 0.5 mm to 5 mm, such as from 0.5 mm to 3 mm, including from 1 mm to 2 mm. In certain instances, the polymeric gel has a length of 1.2 mm. In certain embodiments, the polymeric gel has a depth ranging from 1 μm to 200 μm, such as from 5 μm to 100 μm, including from 10 μm to 50 μm. In some cases, the polymeric gel has a depth of 20 μm.

In certain embodiments, the microfluidic device has a width ranging from 10 cm to 1 mm, such as from 5 cm to 5 mm, including from 1 cm to 5 mm. In some instances, the microfluidic has a length ranging from 100 cm to 1 mm, such as from 50 cm to 1 mm, including from 10 cm to 5 mm, or from 1 cm to 5 mm. In certain aspects, the microfluidic device has an area of 1000 $cm^2$ or less, such as 100 $cm^2$ or less, including 50 $cm^2$ or less, for example, 10 $cm^2$ or less, or 5 $cm^2$ or less, or 3 $cm^2$ or less, or 1 $cm^2$ or less, or 0.5 $cm^2$ or less, or 0.25 $cm^2$ or less, or 0.1 $cm^2$ or less.

In certain embodiments, the microfluidic device is substantially transparent. By "transparent" is meant that a substance allows visible light to pass through the substance. In some embodiments, a transparent microfluidic device facilitates detection of analytes bound to the polymeric medium, for example analytes that include or are labeled with a detectable label, such as a fluorescent label. In some cases, the microfluidic device is substantially opaque. By "opaque" is meant that a substance substantially blocks visible light from passing through the substance. In certain instances, an opaque microfluidic device may facilitate the analysis of analytes that are sensitive to light, such as analytes that react or degrade in the presence of light.

In some aspects, the polymeric medium is provided in an elongated flow path. In these embodiments, the microfluidic device includes a channel, such as a microfluidic channel. The channel may include the polymeric medium as described above. In certain embodiments, the elongated flow path includes an interior volume defined by the sides of the elongated flow path. For example, the elongated flow path may be a channel (e.g., a microfluidic channel), which may define an interior volume of the channel. In certain instances, the polymeric medium is provided in the interior volume of the elongated flow path. For instance, the polymeric medium may be provided in substantially the entire interior volume of the functional region of the elongated flow path. The functional region of the elongated flow path is the region used for assay and detection of the sample constituents and may not include other regions of the elongated flow path, e.g., for sample loading, buffer reservoirs, microfluidic fluid conduits, etc. As described above, the polymeric medium may be provided in substantially the entire interior volume of the functional region of the elongated flow path, such that the polymeric medium substantially fills the width of the interior volume of the elongated flow path. In these embodiments, the polymeric medium substantially fills the interior volume of the elongated flow path, such that there are no significant voids in the interior volume that do not include the polymeric medium. For instance, in these embodiments, the polymeric medium is not a coating on the interior surface of the elongated flow path, but rather the polymeric medium substantially fills the interior volume of the elongated flow path. A polymeric medium that occupies substantially the entire volume of the elongated flow path may provide an increased surface area for immobilization of capture members on the polymeric medium as described above.

In certain embodiments, the microfluidic device does not include a channel that contains the polymeric medium. In these embodiments, the polymeric medium may be provided as a free-standing polymeric medium on a substrate. By "free-standing" is meant that the polymeric medium is associated with a substrate, such as disposed on the surface of the substrate. For instance, the polymeric medium may be disposed on the surface of a substrate such that only one surface (e.g., the bottom surface) of the polymeric medium is in contact with the surface of the substrate. In these instances, the sides of the polymeric medium (e.g., the sides of the polymeric medium extending up from the bottom of the polymeric medium) may not be in contact with the substrate, or a surrounding chamber (e.g., a microfluidic chamber) if present. Similarly, the top surface of the polymeric medium may not be in contact with the substrate, or the surrounding chamber (e.g., a microfluidic chamber) if present. In some instances, the free-standing polymeric medium may be disposed on the surface of a substrate and surrounded by the ambient environment. For example, the polymeric medium may have a bottom surface in contact with the substrate, where the sides of the polymeric medium and the top surface of the polymeric medium are exposed to the ambient environment. In certain embodiments, the free-standing polymeric medium may be disposed on the surface of a substrate and positioned inside an environmental chamber, such that the free-standing polymeric medium is surrounded by the environment provided inside the environmental chamber. In some instances, the polymeric medium may have a bottom surface in contact with the substrate, where the sides of the polymeric medium and the top surface of the polymeric medium are exposed to the environment inside the environmental chamber. For instance, the environmental chamber may contain an environment (e.g., an assay environment) that has a higher humidity than ambient conditions. An assay environment with a higher humidity may facilitate a reduction in evaporation of liquids (e.g., buffers, etc.) from the polymeric medium. In certain embodiments, a free-standing polymeric medium is disposed on a surface of a substrate, where the substrate does not form a channel, a trough or depression around the polymeric medium. Additional aspects of free-standing polymeric media are described in U.S. application Ser. No. 14/271,309, filed May 6, 2014, the disclosure of which is incorporated herein by reference.

Methods

Embodiments of the methods are directed to determining whether an analyte is present in a sample. In certain embodiments of the methods, one or more analytes in the sample may be detected. The method includes introducing a fluid sample into a microfluidic device that includes a polymeric medium as described above. Introducing the fluid sample into the microfluidic device may include contacting the sample with the polymeric medium. In some instances, the sample may be added into a sample reservoir that is in fluid communication with the polymeric medium as described above. In some instances, where the polymeric medium is a free-standing polymeric medium as described above, the sample may be applied to the polymeric medium directly. For example, the sample may be applied to the top surface of the polymeric medium. After applying the sample to the top surface of the polymeric medium, the sample may be allowed to diffuse into the polymeric medium. After sufficient diffusion of the sample into the polymeric medium, excess sample present on the surface of the polymeric medium may be washed off, for example using a washing buffer.

The method further includes moving the sample constituents through the polymeric medium. In some cases, the movement of the sample is produced by gel electrophoresis. In certain cases, the movement of the sample is produced by isoelectric focusing in the polymeric medium. In certain embodiments, moving the sample constituents through the polymeric medium includes applying a directional electric field to the polymeric medium in a manner sufficient to move components of the sample through the polymeric medium. In certain embodiments, movement of the sample through the polymeric medium is achieved by passive diffusion as described above. The sample may include distinct detectable analytes, where each analyte binds to a different capture member in the polymeric medium.

As the constituents in the sample move through the polymeric medium, a specific analyte of interest may be specifically bound by a capture member in the polymeric medium. For example, as described herein, the capture member may include an antigen, and as the constituents in the sample move through the polymeric medium, a specific antibody of interest (or fragment thereof) may bind to the antigen and become immobilized in the polymeric medium due to the specific binding interaction. In some cases, the immobilized analyte may then be detected. For instance, the method may include obtaining a signal from the analyte detection domain (i.e., the region of the polymeric medium that includes the capture member) to determine whether the analyte of interest is bound to the polymeric medium in the analyte detection domain, and thus was present in the sample.

In certain embodiments, the method includes determining whether an analyte of interest is present in a sample, e.g., determining the presence or absence of one or more analytes of interest in a sample. In some instances, the microfluidic devices are configured to detect the presence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, such as low, medium, high (e.g., low, medium, or high concentration of the analyte of interest in the sample), is provided to a user regarding the amount of analyte in the sample and fine scale results in which a measurement of the concentration of the analyte is provided to the user.

In certain embodiments, the method includes evaluating the polymeric medium for the presence of the analyte or analytes of interest (e.g., the two or more analytes of interest). For example, the method may include detecting an analyte of interest bound to the polymeric medium. Detectable binding of an analyte of interest to the polymeric medium indicates the presence of the analyte of interest in the sample. Moieties not of interest that traverse the polymeric medium and do not bind to the capture members in the polymeric medium may be washed away or transferred to a secondary analysis device such as, but is not limited to, a UV spectrometer, and IR spectrometer, a mass spectrometer, an HPLC, an affinity assay device, and the like.

In some instances, the analyte of interest includes a detectable label. The detectable label may include, but is not limited to, a fluorescent label, a colorimetric label, a chemiluminescent label, multicolor reagents, enzyme-linked reagents, avidin-streptavidin associated detection reagents, radiolabels, gold particles, magnetic labels, and the like. In some instances, the label is covalently bound to the analyte of interest. For instance, prior to analysis in the microfluidic device, a sample may be contacted with a detectable label that binds to one or more analytes of interest.

In certain embodiments, detecting the analyte of interest includes contacting the analyte of interest with a label configured to specifically bind to the analyte of interest (e.g., a secondary specific binding member, such as a secondary antibody, that specifically binds to the analyte of interest). For example, detecting the analyte of interest may include contacting the analyte of interest with a secondary specific binding member that specifically binds to the analyte of interest. In certain instances, the label may include a detectable label, such as, but not limited to, a fluorescent label, a colorimetric label, a chemiluminescent label, multicolor reagents, enzyme-linked reagents, avidin-streptavidin associated detection reagents, radiolabels, gold particles, magnetic labels, and the like.

In certain embodiments, the method includes enhancing the detectable signal from a labeled analyte of interest. For instance, enhancing the detectable signal from a labeled analyte of interest may include contacting a labeled analyte of interest with a secondary label configured to specifically bind to the labeled analyte of interest. In certain instances, the secondary label is a secondary specific binding member, such as a secondary antibody, that specifically binds to the labeled analyte of interest. As such, enhancing the detectable signal from the labeled analyte of interest may include contacting the labeled analyte of interest with a secondary specific binding member configured to specifically bind to the labeled analyte of interest. The use of two or more detectable labels as described above may facilitate the detection of the analyte of interest by improving the signal-to-noise ratio.

The secondary label can be any molecule that specifically binds to a protein or nucleic acid sequence or biomacromolecule that is being targeted (e.g., the analyte of interest). Depending on the nature of the analyte, the label can be, but is not limited to: antibodies against an epitope of a peptidic analyte (e.g., an antibody or fragment thereof); or any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the label includes a secondary antibody. The secondary antibody may specifically bind to the analyte of interest.

In certain embodiments, the secondary label includes a detectable label. Detectable labels include any convenient label that may be detected using the methods and systems, and may include, but are not limited to, fluorescent labels, colorimetric labels, chemiluminescent labels, multicolor reagents, enzyme-linked reagents, avidin-streptavidin associated detection reagents, radiolabels, gold particles, magnetic labels, and the like. In certain embodiments, the secondary label includes a secondary antibody associated with a detectable label. For example, the secondary label may include a labeled antibody (e.g., a fluorescently labeled antibody) that specifically binds to a labeled analyte of interest.

In some embodiments, the analyte of interest can be identified so that the presence of the analyte of interest can then be detected. For instance, the method may include evaluating the polymeric medium for the presence of two or more analytes. Analytes may be identified by any of the methods described herein. For example, a labeling agent, such as an analyte specific binding member that includes a detectable label may be employed, as described above. In certain embodiments, the detectable label is a fluorescent label. Fluorescent labels are labeling moieties that are detectable by a fluorescence detector. For example, binding of a fluorescent label to an analyte of interest may allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoyl carbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl) aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propionic acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular weight, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 2 to 50 distinct analytes, including 2 to 20 distinct analytes, or 2 to 10 distinct analytes of interest.

In certain embodiments, multiplex analysis also includes the use of two or more different detectable labels. The two or more different detectable labels may specifically bind to the same or different analytes. In some cases, the two or more different detectable labels may specifically bind to the same analyte. For instance, the two or more different detectable labels may include different antibodies specific for different epitopes on the same analyte. The use of two or more detectable labels specific for the same analyte may facilitate the detection of the analyte by improving the signal-to-noise ratio. In other cases, the two or more different detectable labels may specifically bind to different analytes. For example, the two or more detectable labels may include different antibodies specific for epitopes on different analytes. The use of two or more detectable labels each specific for different analytes may facilitate the detection of two or more respective analytes in the sample in a single assay.

In certain embodiments, the method is an automated method. As such, the method may include a minimum of user interaction with the microfluidic devices and systems after introducing the sample into the microfluidic device. For example, the step of directing the sample through the polymeric medium may be performed by the microfluidic device and system, such that the user need not manually perform this step. In some cases, the automated method may facilitate a reduction in the total assay time. For example, embodiments of the method may be performed in 120 min or less, or 90 min or less, or 60 min or less, such as 45 min or less, or 30 min or less, such as 20 min or less, including 15 min or less, or 10 min or less, or 5 min or less.

Samples that may be assayed with the subject methods may include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analyte of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular mass, size, charge, isoelectric point, etc.).

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. In some instances, the sample of interest is a blood product, such as whole blood, serum, plasma, etc. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to proteins and peptides, with or without modifications, e.g., antibodies, diabodies, Fab fragments, DNA or RNA binding proteins, phosphorylated proteins (phosphoproteomics), peptide aptamers, epitopes, combinations thereof, and the like.

In certain embodiments, the method is configured to detect constituents of interest in a sample, where the sample size is small. For example, the method may be configured to detect constituents of interest in a sample, where the sample size is 1 mL or less, such as 750 µL or less, including 500 µL or less, or 250 µL or less, of 100 µL or less, or 75 µL or less, or 50 µL or less, or 40 µL or less, or 30 µL or less, or 20 µL or less, or 10 µL or less, or 5 µL or less, or 1 µL or less, or 750 nL or less, or 500 nL or less, or 250 nL or less, or 100 nL or less, or 75 nL or less, or 50 nL or less, or 25 nL or less, or 10 nL or less, or 5 nL or less, or 1 nL or less. In some instances, the method is configured to detect constituents of interest in a sample, where the sample size is 100 nL or less.

In certain embodiments, the method includes concentrating, diluting, or buffer exchanging the sample prior to directing the sample through the separation medium. Concentrating the sample may include contacting the sample with a concentration medium prior to contacting the sample with the polymeric medium. The concentration medium may include a small pore size polymeric gel, a membrane (e.g., a size exclusion membrane), combinations thereof, and the like. Concentrating the sample prior to contacting the sample with the polymeric medium may facilitate a decrease in the amount of concentrated sample used in an assay and/or may facilitate a decrease in the total assay time. Diluting the sample may include contacting the sample with additional buffer prior to contacting the sample with the polymeric medium. Buffer exchanging the sample may include contacting the sample with a buffer exchange medium prior to contacting the sample with the polymeric medium. The buffer exchange medium may include a buffer different from the sample buffer. The buffer exchange medium may include, but is not limited to, a molecular sieve, a porous resin, and the like.

In certain embodiments, the method does not include a blocking step. As such, methods of the present disclosure may not include a step of contacting the polymeric medium with a blocking reagent prior to detecting the analyte of interest. In some cases, a blocking step is not needed to minimize non-specific binding of analytes to the polymeric medium. For example, a blocking step may not be necessary because the analyte of interest (e.g., antibody) specifically binds only to regions of the polymeric medium that include the specific capture member (e.g., antigen) that the analyte of interest binds to.

In certain embodiments, the method includes optional washing steps, which may be performed at various times before, during and after the other steps in the method. For example, a washing step may be performed after binding the capture member to the polymeric medium, after contacting the sample with the polymeric medium, after contacting the polymeric medium-bound analyte of interest with a secondary label, etc.

Embodiments of the method may also include releasing the analyte bound to the polymeric medium. The releasing may include contacting the bound analyte with a releasing agent. The releasing agent may be configured to disrupt the binding interaction between the analyte and the polymeric medium. In some cases, the releasing agent is a reagent, buffer, or the like, that disrupts the binding interaction between the analyte and the capture member of the polymeric medium causing the capture member to release the analyte. After releasing the analyte from the polymeric medium, the method may include transferring the analyte away from the polymeric medium. For example, the method may include directing the released analyte downstream from the polymeric medium for secondary analysis with a secondary analysis device such as, but is not limited to, a UV spectrometer, and IR spectrometer, a mass spectrometer, an HPLC, an affinity assay device, a second microfluidic device as described herein, and the like.

Aspects of embodiments of the methods may also include methods of producing a polymeric medium. The method of producing the polymeric medium may include providing precursor moieties that are then formed into the polymeric medium. For example, the method of producing the polymeric medium may include providing precursor moieties in a flow path of the microfluidic device. In some instances, the flow path is filled with the precursor moieties (e.g., gel precursors, such as polyacrylamide gel precursors). In some cases, the method includes activating the precursor moieties to form the polymeric medium. For example, activating the polymeric medium precursor moieties may include chemically activating the precursor moieties by contacting the precursor moieties with an activation agent, such as, but not limited to, a peroxide. In certain cases, activating the precursor moieties includes photo-activating the precursor moieties by contacting the precursor moieties with light. As described above, the light used to activate formation of the polymeric medium may have a wavelength of blue light in the visible spectrum. For instance, the light used to activate formation of the polymeric medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the polymeric medium has a wavelength ranging from 465 to 475 nm. In some instances, the light used to activate formation of the polymeric medium has a wavelength of 470 nm. In certain embodiments, the wavelength of light used to activate formation of the polymeric medium is different from the wavelength of light used to covalently bond the capture member to the polymeric medium as described above.

In certain embodiments, the method of producing a microfluidic assay device includes producing a polymeric medium in a flow path as described above. The polymeric medium may include distinct analyte detection domains having functional groups that covalently bond to a capture member upon application of an applied stimulus, as described herein. The method also includes introducing into the polymeric medium a capture member that specifically binds to an analyte of interest, and exposing a region of the polymeric medium to the applied stimulus to produce an analyte detection domain that includes the capture member covalently bound to the polymeric medium. For example, the method may include introducing into the polymeric medium a first capture member that specifically binds to a first analyte, and exposing a first region of the polymeric medium to the applied stimulus to produce a first analyte detection domain that includes the first capture member covalently bound to the polymeric medium. Embodiments of the method also include introducing into the polymeric medium a second capture member that specifically binds to a second analyte, and exposing a second region of the flow path to the applied stimulus to produce a second analyte detection domain that includes the second capture member covalently bound to the polymeric medium. In this manner, multiple analyte detection domains can be produced in a single polymeric medium.

In certain embodiments, the capture member may be applied to the polymeric medium by contacting the capture member with the polymeric medium. In some instances, the capture member may be added into a reservoir that is in fluid communication with the polymeric medium as described above (e.g., the sample reservoir described herein may be used to introduce the capture member to the polymeric medium). In some instances, where the polymeric medium is a free-standing polymeric medium as described above, the capture member may be applied to the polymeric medium directly. For example, the capture member may be applied to the top surface of the polymeric medium. After applying the capture member to the top surface of the polymeric medium, the capture member may be allowed to diffuse into the polymeric medium. After sufficient diffusion of the capture member into the polymeric medium, excess capture member present on the surface of the polymeric medium may be washed off, for example using a washing buffer.

In some instances, the method further includes moving the capture member through the polymeric medium. In some cases, the movement of the capture member is produced by electrophoresis, such as by applying a directional electric field to the polymeric medium in a manner sufficient to move the capture member through the polymeric medium. In certain embodiments, movement of the capture member through the polymeric medium is achieved by passive diffusion as described above. Once sufficient movement of the capture member into the polymeric medium (e.g., into the desired analyte detection domain(s)) has been achieved, the polymeric medium may be exposed to an applied stimulus to covalently bond the capture member to the polymeric medium as described herein. The applied stimulus may be electromagnetic radiation (e.g., light, such as UV light). As such, the method may include exposing the polymeric medium to the applied stimulus through a mask, such as a photomask. The photomask may block light from contacting certain areas of the polymeric medium, while allowing certain areas (e.g., the analyte detection domain(s)) to be exposed to the light, thus covalently bonding the capture members to the polymeric medium only in the desired analyte detection domain(s).

After covalent bonding of the capture member to the polymeric medium in the analyte detection domain, the unbound capture member may be washed away from the polymeric medium, such as by flowing a washing buffer through and/or over the polymeric medium. Additional capture member, such as a capture member different from the first capture member) may be applied to the polymeric medium as described above to form another analyte detection domain that is distinct from the first analyte detection domain. The steps of introducing a capture member to the polymeric medium, exposing the polymeric medium to an applied stimulus to covalently bond the capture member to the polymeric medium, and washing unbound capture member from the polymeric medium can be repeated as desired to produce multiple distinct analyte detection domains in the polymeric medium.

In other embodiments, a mixture of capture members may be introduced into the polymeric medium substantially simultaneously. For instance, two or more capture members (e.g., two or more different capture members) may be obtained separately and then mixed together. The mixture of capture members then may be applied to the polymeric medium to produce distinct analyte detection domains. For example, the mixture of capture members may be applied to the polymeric medium by adding the mixture to a reservoir in fluidic communication with the polymeric medium, or by applying the mixture to a top surface of a free-standing polymeric medium as described above. The mixture of capture members may then be separated in the polymeric medium, such as by gel electrophoresis, isoelectric focusing, etc., such that distinct bands of different capture members are produced in the polymeric medium. The polymeric medium may be exposed to an applied stimulus (e.g., light, such as UV light) to covalently bond the bands of capture members to the polymeric medium to produce the distinct analyte detection domains. In certain embodiments, exposing the polymeric medium to the applied stimulus may be performed without using a photomask because the capture members have already been separated into distinct bands of capture members in the polymeric medium. In some instances, a mixture of capture members as described above finds use in a multiplex ELISA assay protocol.

In other embodiments, the mixture of capture members may be obtained as a mixture, such as a mixture of variants of a capture member (e.g., a mixture of antigen variants). The mixture of capture members may be applied to the polymeric medium as described above, such as by adding the mixture to a reservoir in fluidic communication with the polymeric medium, or by applying the mixture to a top surface of a free-standing polymeric medium. As described above, the mixture of capture members may then be separated in the polymeric medium, such as by gel electrophoresis, isoelectric focusing, etc., such that distinct bands of different capture members are produced in the polymeric medium. The polymeric medium may be exposed to an applied stimulus (e.g., light, such as UV light) to covalently bond the bands of capture members to the polymeric medium to produce the distinct analyte detection domains. In certain embodiments, exposing the polymeric medium to the applied stimulus may be performed without using a photomask because the capture members have already been separated into distinct bands of capture members in the polymeric medium. In some instances, a mixture of capture members as described above finds use in a Western blot assay protocol.

Systems

Aspects of certain embodiments include a system for determining whether an analyte is present in a sample. In some instances, the system includes a microfluidic device as described herein. In certain embodiments, the system also includes a detector. In some cases, the detector is a detector configured to detect a detectable label. The detector may include any type of detector configured to detect the detectable label used in the assay. As described above, detectable label may be a fluorescent label, colorimetric label, chemiluminescent label, multicolor reagent, enzyme-linked reagent, avidin-streptavidin associated detection reagent, radiolabel, gold particle, magnetic label, etc. In some instances, the detectable label is a fluorescent label. In these instances, the detector may be configured to contact the fluorescent label with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected by the detector to determine the presence of the labeled analyte bound to the separation medium.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

The system may also include a source of electromagnetic radiation (i.e., an electromagnetic radiation source). In some cases, the electromagnetic radiation source is a light source. For example, the light source may include a visible light source, a UV light source, an infrared light source, etc. In some instances, the electromagnetic radiation source includes a light source, such as a UV light source. As described above, the electromagnetic radiation source may be used to apply electromagnetic radiation to polymeric medium precursor moieties in the microfluidic device to produce the polymeric medium. As described above, the electromagnetic radiation source may be used to apply electromagnetic radiation to the polymeric medium in the microfluidic device to covalently bond a capture member to the polymeric medium during fabrication of the polymeric medium.

Systems of the present disclosure may include various other components as desired. For example, the systems may include fluid handling components, such as microfluidic fluid handling components. The fluid handling components may be configured to direct one or more fluids through the microfluidic device. In some instances, the fluid handling components are configured to direct fluids, such as, but not limited to, fluid samples, buffers (e.g., electrophoresis buffers, wash buffers, release buffers, etc.), and the like. In certain embodiments, the microfluidic fluid handling components are configured to deliver a fluid to the polymeric medium of the microfluidic device, such that the fluid contacts the polymeric medium. The fluid handling components may include microfluidic pumps. In some cases, the microfluidic pumps are configured for pressure-driven microfluidic handling and routing of fluids through the microfluidic devices and systems disclosed herein. In certain instances, the microfluidic fluid handling components are configured to deliver small volumes of fluid, such as 1 mL or less, such as 500 μL or less, including 100 μL or less, for example 50 μL or less, or 25 μL or less, or 10 μL or less, or 5 μL or less, or 1 μL or less.

In certain embodiments, the systems include one or more electric field generators. An electric field generator may be configured to apply an electric field to various regions of the microfluidic device. The system may be configured to apply an electric field such that the sample is electrokinetically transported through the microfluidic device. For example, the electric field generator may be configured to apply an electric field to the polymeric medium. In some cases, the applied electric field may be aligned with the directional axis of the polymeric medium. As such, the applied electric field may be configured to electrokinetically transport the analytes and components in a sample through the polymeric medium. In some instances, the electric field generators are configured to apply an electric field with a strength ranging from 10 V/cm to 1000 V/cm, such as from 100 V/cm to 800 V/cm, including from 200 V/cm to 800 V/cm, or from 400 v/cm to 800 V/cm.

In certain embodiments, the subject system is a biochip (e.g., a biosensor chip). By "biochip" or "biosensor chip" is meant a microfluidic system that includes a substrate surface which displays two or more distinct microfluidic devices on the substrate surface. In certain embodiments, the microfluidic system includes a substrate surface with an array of microfluidic devices.

An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., devices) may be separated by intervening spaces. Any given substrate may carry one, two, four or more arrays disposed on a front surface of the substrate. Depending upon the use, any or all of the arrays may be the same or different from one another and each may contain multiple distinct microfluidic devices. An array may contain one or more, including two or more, four or more, eight or more, 10 or more, 25 or more, 50 or more, or 100 or more microfluidic devices. In certain embodiments, the microfluidic devices can be arranged into an array with an area of 100 cm$^2$ or less, 50 cm$^2$ or less, or 25 cm$^2$ or less, 10 cm$^2$ or less, 5 cm$^2$ or less, such as 1 cm$^2$ or less, including 50 mm$^2$ or less, 20 mm$^2$ or less, such as 10 mm$^2$ or less, or even smaller. For example, microfluidic devices may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less.

Arrays of microfluidic devices may be arranged for the multiplex analysis of samples. For example, multiple microfluidic devices may be arranged in series, such that a sample may be analyzed for the presence of several different analytes in a series of microfluidic devices. In certain embodiments, multiple microfluidic devices may be arranged in parallel, such that two or more samples may be analyzed at substantially the same time.

Aspects of the systems include that the microfluidic devices may be configured to consume a minimum amount of sample while still producing detectable results. For example, the system may be configured to use a sample volume of 100 μL or less, such as 75 μL or less, including 50 μL or less, or 25 μL or less, or 10 μL or less, for example, 5 μL or less, 2 μL or less, or 1 μL or less while still producing detectable results. In certain embodiments, the system is configured to have a detection sensitivity of 1 nM or less, such as 500 pM or less, including 100 pM or less, for instance, 1 pM or less, or 500 fM or less, or 250 fM or less, such as 100 fM or less, including 50 fM or less, or 25 fM or less, or 10 fM or less. In some instances, the system is configured to be able to detect analytes at a concentration of 1 μg/mL or less, such as 500 ng/mL or less, including 100 ng/mL or less, for example, 10 ng/mL or less, or 5 ng/mL or less, such as 1 ng/mL or less, or 0.1 ng/mL or less, or 0.01 ng/mL or less, including 1 μg/mL or less. In certain embodiments, the system has a dynamic range from $10^{-18}$ M to 10 M, such as from $10^{-15}$ M to $10^{-3}$ M, including from $10^{-12}$ M to $10^{-6}$ M.

In some cases, the system is configured to have a signal-to-noise ratio (SNR) of 10 or more, such as 15 or more, including 20 or more, or 30 or more, or 40 or more, or 50 or more, or 60 or more, or 70 or more, or 80 or more, or 90 or more, or 100 or more, or 150 or more, or 200 or more, or 500 or more, or 1,000 or more, or 2,000 or more, or 3,000 or more, or 4,000 or more, or 5,000 or more, or 6,000 or more, or 7,000 or more, or 8,000 or more, or 9,000 or more, or 10,000 or more. In some cases, the achievable signal-to-noise ratio depends on the method of detection used in the assay. For example, in certain embodiments the analyte of interest is directly labeled with a detectable label. In these embodiments, the signal-to-noise ratio may be 10 or more, such as 15 or more, including 20 or more, or 30 or more, or 40 or more, or 50 or more, or 60 or more, or 70 or more, or 80 or more, or 90 or more, or 100 or more, or 150 or more, or 200 or more. In other embodiments, the analyte of interest is first labeled with a primary label (e.g., a primary antibody) and then the primary label is labeled with a secondary label (e.g., a secondary antibody). In these embodiments, the signal-to-noise ratio may be 100 or more, such as 150 or more, including 200 or more, or 500 or more, or 1,000 or more, or 2,000 or more, or 3,000 or more, or 4,000 or more, or 5,000 or more, or 6,000 or more, or 7,000 or more, or 8,000 or more, or 9,000 or more, or 10,000 or more.

In certain embodiments, the microfluidic devices are operated at a temperature ranging from 1° C. to 100° C., such as from 5° C. to 75° C., including from 10° C. to 50° C., or from 20° C. to 40° C. In some instances, the microfluidic devices are operated at a temperature ranging from 35° C. to 40° C.

Utility

Embodiments of the devices, systems and methods of the present disclosure find use in accurate photo-patterning of a capture member inside a polymeric medium for the fabrication of assay platforms that can be used to identify pathogens, immune reactions or presence of biochemical agents. The ability to define distinct regions inside microfluidic devices serves as the basis for a variety of analytical platforms. Distinct, heterogeneous regions may be used to perform multiplexed assays and experiments. The localized patterning of capture members may be used to produce bioanalytical devices.

The devices, systems and methods of the present disclosure find use in the detection of analytes of interest, such as proteins, peptides (e.g., antibodies, or fragments thereof), nucleic acids, and the like. In some cases, the subject devices, systems and methods find use in the detection of proteins or peptides, such as, but not limited to antibodies or fragments thereof.

In certain embodiments, the subject devices, systems and methods find use in the detection of proteins, or other biomolecules in a sample. The methods may include the detection of a set of biomarkers, e.g., two or more distinct protein biomarkers, in a sample. For example, the methods may be used in the rapid, clinical detection of two or more disease biomarkers in a biological sample, e.g., as may be employed in the diagnosis of a disease condition in a subject, or in the ongoing management or treatment of a disease condition in a subject, etc. In addition, the subject devices, systems and methods may find use in protocols for the detection of an analyte in a sample, such as, but not limited to, Western blotting, and the like.

In certain embodiments, the subject devices, systems and methods find use in detecting biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like. In some instances, the subject devices, systems and methods may be used to detect the presence or absence of particular biomarkers, as well as an increase or decrease in the concentration of particular biomarkers in a blood product, such as whole blood, serum, plasma, etc.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods find use in portable and point-of-care or near-patient molecular diagnostics.

In certain embodiments, the subject devices, systems and methods find use in detecting biomarkers for a disease or disease state. In certain instances, the subject devices, systems and methods find use in detecting biomarkers for the characterization of cell signaling pathways and intracellular communication for drug discovery and vaccine development. For example, the subject devices, systems and methods may be used to detect and/or quantify the amount of biomarkers in diseased, healthy or benign samples. In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like.

The subject devices, systems and methods find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time. For example, the subject devices, systems and methods find use in affinity reagent screening. High-throughput microfluidic devices that include a polymeric medium as described herein may be used to select biomarker isoform-specific affinity reagents, such as specific monoclonal antibodies. Such reagents may be used in ELISA assays for disease-specific biomarker isoforms present in clinical proteinaceous samples. In some cases, reagents may be screened in serial or for their multiplexed (parallel) capability for highly specific binding.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the mass and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a microfluidic device as described in detail herein. Embodiments of the kits also include a packaging configured to contain the microfluidic device. The packaging may be a sealed packaging. For example, in certain embodiments, the kits include a sealed package configured to maintain the sterility of the microfluidic device. The sealed package may be sealed such that substantially no external contaminants, such as dirt, microbes (e.g., fungi, bacteria, viruses, spore forms, etc.), liquids, gases, and the like, are able to enter the sealed package. For example, the sealed package may be sealed such the package is water-tight and/or air-tight.

The kits may further include a buffer. For instance, the kit may include a buffer, such as an electrophoretic buffer, a sample buffer, and the like. The kits may further include additional reagents, such as but not limited to, release agents, denaturing agents, refolding agents, detergents, detectable labels (e.g., fluorescent labels, colorimetric labels, chemiluminescent labels, multicolor reagents, enzyme-linked reagents, avidin-streptavidin associated detection reagents, radiolabels, gold particles, magnetic labels, etc.), and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

Introduction

Experiments were performed to produce microfluidic channels with three-dimensional photocapture of proteins that can be completed in a single step with no additional linker molecules required. Experiments were also performed to verify the ability of the photopatterned proteins to selectively capture antibodies using BSA/anti-BSA antibody pair. Experiments were also performed demonstrating a HCV diagnostic device based on the embodiments of the present disclosure and showing that the device was capable of assaying human sera to positively identify HCV+ human patient serum samples.

A light-activated volume-accessible gel (LAVAgel) was used as the functional matrix for the assay. The LAVAgel, produced by incorporating N-[3-[(4-benzoylphenyl) formamido[propyl]methacrylamide (BPMAC) into a polyacrylamide (PA) gel matrix, produced a PA gel that included a photo-activatable covalent capture capability. When illuminated by UV, the activated gel covalently linked to targets in proximity of the benzophenone group of BPMAC. For example, when used as a matrix for performing protein separation (e.g., isoelectric focusing), the matrix allowed the separated proteins to be held in place through photocapture. This enabled an immunoblotting step to be performed in situ, without the need for a transfer step (e.g., transfer to a separate blotting membrane).

The LAVAgel matrix was a photopatternable substrate and was used for the fabrication of three-dimensional captured protein bands. The use of LAVAgel as the substrate allowed the photocapture chemistry to be directly incorporated into the substrate, and thus obviated the need for any modification steps that were required in other patterning methods. In addition, there was minimal nonspecific interaction of proteins with the PA gel, and thus there was no need for any blocking step. This combined with the incorporation of the BPMAC into the gel matrix, simplified the preparation of the substrate. Unlike methods that require either grafting or pre-patterning of capture moieties, the use of LAVAgel reduced photopatterning to a single-step process. The use of polyacrylamide gel as a nanoporous matrix also resulted in a significantly higher effective capture surface area when compared to channel surface immobilization techniques. For example, the LAVAgel provided at least two orders-of-magnitude increase in capture efficiency compared to the inner surface of a capillary. Finally, despite the presence of a nanoporous matrix, the use of electrokinetic transport overcame the fluidic resistance present in substrates, such as dense monoliths. This allowed for short diffusion distances in the system to achieve both efficient photocapture of proteins and subsequent reaction with introduced samples.

LAVAgel was also used as a photopatterning substrate to fabricate a microfluidic multiplexed HCV diagnostic device that was capable of assaying human sera and identifying HCV+ patient serum samples. The polymeric LAVAgel medium of the present disclosure finds use in a robust and facile method for fabricating complex patterns in microfluidic devices that have broad applications in the field of bioanalytical tools.

Chemicals and Reagents

Aqueous solution of 30% (w/v) (29:1) acrylamide/bis-acrylamide, glacial acetic acid, ammonium persulfate (APS), N,N,N',N'-tetramethylethylenediamine (TEMED), methanol and 3-(trimethoxysilyl)-propyl methacrylate and sodium hydroxide (NaOH) were purchased from Sigma-Aldrich (St. Louis, Mo.). N-[3-[(4-benzoylphenyl) formamido[propyl]methacrylamide (BPMAC) was obtained from PharmAgra Labs (Brevard, N.C.). AlexaFluor 488 (AF488) and AlexaFluor 555 (AF555) labeled Ovalbumin (OVA) and bovine serum albumin (BSA) were purchased from Life Technologies (Carlsbad, Calif.). FITC-labelled anti-BSA antibody was purchased from MyBiosource Inc. (San Diego, Calif.). Hepatitis-C Virus (HCV) positive serum, AF488 conjugated HCV Core(c22p), NS3(c33c) and NS4(c100p) antigens were provided by Norvartis Diagnostics (Emeryville, Calif.). HCV negative human sera were purchased from SeraCare Life Sciences (Oceanside, Calif.). AlexaFluor 568 (AF568) conjugated secondary goat anti-human antibody was purchased from Life Technologies (Carlsbad, Calif.). All antigen, antibody and serum samples were diluted into 1× Tris-Glycine buffer before introduction into the chip. 1× Tris-Glycine buffer was purchased at 10× concentration from Bio-Rad (Hercules, Calif.).

Data Acquisition, Control and Patterning Instrumentation

Images were acquired on an Olympus IX-50 inverted fluorescence microscope (Olympus USA, Center Valley, Pa.) using a Peltier-cooled CCD camera CoolSNAP HQ2 (Roper Scientific, Trenton, N.J.) through a 10× objective. Green fluorescent channel (AlexFluor 488) and red fluorescent channel (AlexaFluor 568) exposure times were 150 ms and 300 ms, respectively, unless otherwise specified. Illumination was provided by X-cite Exacte illumination system from Lumen Dynamics (Mississauga, Canada) controlled using Metamorph software from Molecular Devices (Sunnyvale, Calif.). Image analysis was performed using ImageJ from NIH (Bethesda, Md.). Custom-built programmable high-voltage power supply (HVPS) was used for electrophoretic control with platinum electrodes directly inserted into the sample reservoir wells. UV for photopatterning was provided by a Hamamatsu Lightningcure LC5 unit (Bridgewater, N.J.) through a Lumatec series 380 liquid light guide (Deisenhofen, Germany). Photomasks designs were produced in-house and laser cut from 50 μm thick stainless steel sheet using Universal Laser PLS6MW with a 30 W fiber laser cartridge (Scottsdale, Ariz.).

Microfluidic Chip Preparation

Chip designs were performed in-house and fabrication was performed by Caliper Life Sciences (Hopkinton, Mass.). Standard wet etching and drilling methods were used followed by thermal bonding. Each device included 3 parallel microfluidic channels of 1.2 mm length, 90 μm width and 20 μm depth connecting wells of 2 mm in diameter and 1 mm deep that served as the sample reservoirs. Each chip contained 4 devices with 3 channels each.

Prior to introduction of polyacrylamide gel precursor solutions, the glass channel surfaces were functionalized with an acrylate-terminated self-assembled monolayer. Precursor solution with 1×TG, 4% wt/vol total acrylamide (4% T) with 2.6% of the total as cross-linker bisacrylamide (2.6% C) and 1.6 nM BPMAC were mixed and degassed with sonication and vacuum. The BPMAC produced a polyacrylamide gel that had a photo-activatable capture capability. Immediately prior to introduction into the device, 0.08% (wt/vol) of APS and 0.08% (vol/vol) of TEMED were added to the precursor solution to initiate polymerization. Wells were flushed twice with 1×TG buffer after 15 min of polymerization, and then filled with 1× Tris-Glycine (TG) buffer and stored in a humidified petri dish at 4° C. Gelation was confirmed by examining excess precursor solutions prior to well rinsing.

Barcode Assay Fabrication

Photopatterning of proteins bands (barcodes) inside the microfluidic channels was performed after completion of chip preparation. Proteins to be immobilized (labeled or unlabeled) were diluted into 1×TG buffer prior to pipetting into the sample wells (~6 μL). The samples were then electrophoretically loaded into the microfluidic channel by applying a 200V electrical bias between the sample and sink wells. Barcode proteins were loaded for two minutes which was empirically derived to be the time required for proteins to be evenly loaded into the channels. After loading, the photomask was placed on top of the channels and the light guide was placed directly on top of the opening in the mask. Subsequently, UV illumination was applied for five seconds at 20% diaphragm opening controlled through the instrument interface. After illumination, the wells were each rinsed three times with 1×TG buffer and a reverse bias of 500V was applied for five minutes to electrophoretically wash out non-immobilized proteins. Confirmation of successful protein band patterning through fluorescence imaging was performed.

HCV Diagnostic Assay Operation

Sample reservoirs were rinsed with 1×TG buffer three times before serum samples were pipetted onto the chip. Serum samples were electrophoretically introduced into the microfluidic channels to be assayed. Diluted serum samples (1:40) were introduced continuously for fifteen minutes at 200V bias followed by an electrophoretic washout step at 200V reverse bias for twenty minutes. Immunoprobing of captured human anti-HCV antibodies was performed by introducing fluorescently labeled anti-human antibodies for ten minutes at 200V bias followed by washout at 200V for an additional ten minutes. The blotting result was then captured as fluorescent images.

Results and Discussion

Photopatterned Barcodes for a Microfluidic Sandwich Assay

The barcode assay platform described herein was used in a single LAVAgel-filled microfluidic channel. FIG. 1 (panel A) shows a schematic of a photopatterned barcode device. The red (darker shaded) sections indicate regions in which proteins were immobilized and blue (lighter shaded) regions indicate regions with no immobilized proteins. The enlarged inset schematic of FIG. 1 (panel A) shows the edge of a patterned band. As can be seen in the enlargement, the entire volume of the polyacrylamide gel is functionalized with BPMAC linked into the polyacrylamide gel matrix (thin lines). The proteins however are localized to a select region and are immobilized onto the gel matrix through conjugation with the BPMAC. As discussed above, the BPMAC provides for a polyacrylamide gel with photo-capture capabilities. The methacrylic acid moiety of the BPMAC (FIG. 1 (panel B)) allowed the molecule to be crosslinked into the polyacrylamide gel matrix during free radical polymerization of the precursor solution into the hydrogel state. The benzophenone group was then activated by UV light to form covalent bonds with nearby targets that were introduced subsequent to gel formation. The photocapture chemistry was utilized to create a microfluidic sandwich assay as shown in FIG. 1 (panel C). Antigens were immobilized in the polyacrylamide gel using BPMAC through photopatterning. Unlabelled primary antibodies that were the assay targets were electrophoretically introduced into the device. Through specific antibody/antigen interactions the immobilized antigens captured the introduced primary antibodies. In some instances, labeled secondary antibodies were then introduced to identify the presence of the captured primary antibodies.

Complex Patterns Generation Through Photopatterning

Figure 2:
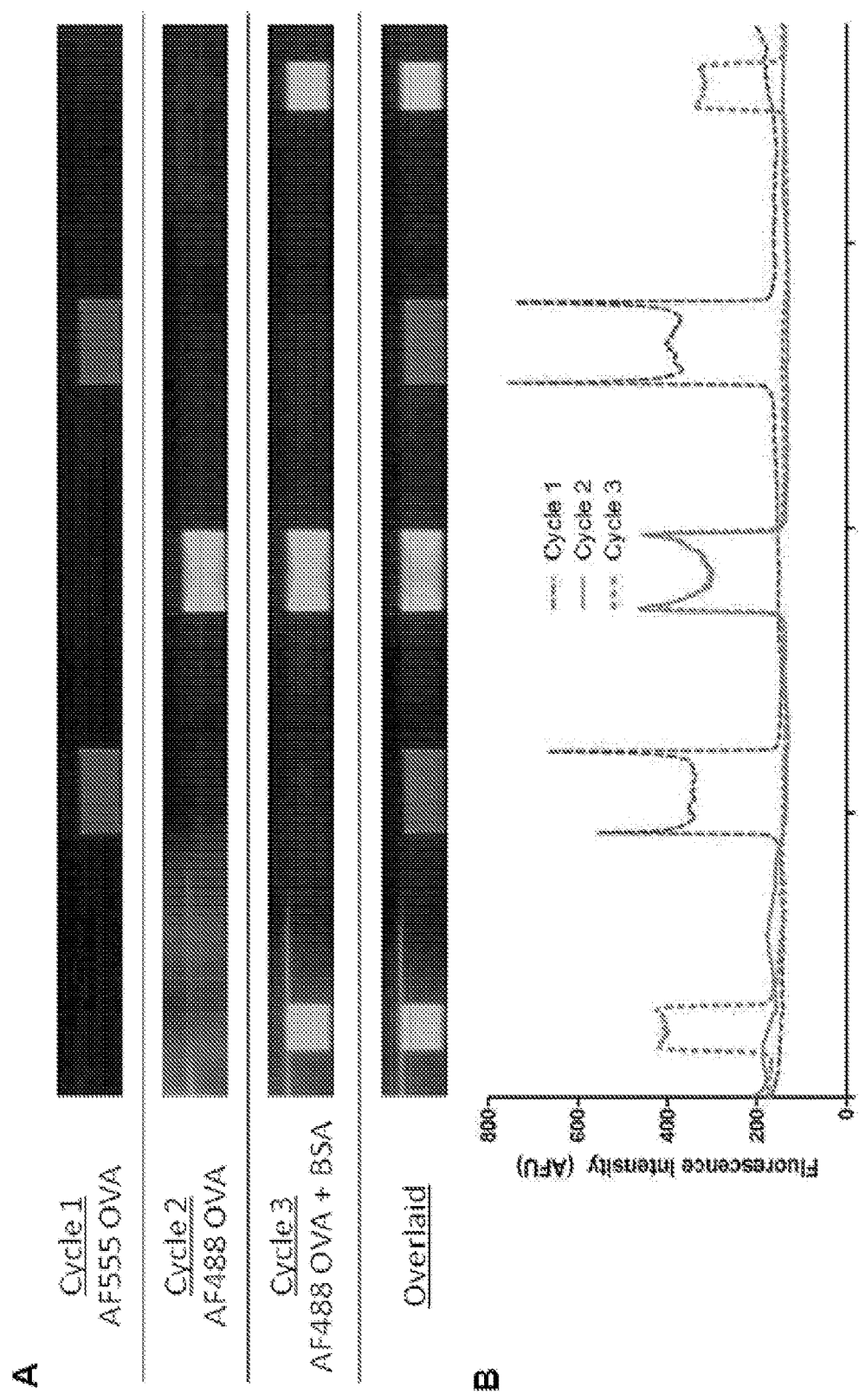
FIG. 2 (panel A) shows steps in a process of fabricating a 5-band pattern in a microfluidic channel using three distinct fluorescently labeled proteins in three patterning cycles, according to embodiments of the present disclosure.

For the fabrication of the barcode patterns, proteins introduced into the gel-filled channel were covalently linked to the matrix at selected regions through the benzophenone chemistry when UV light was applied. The ability to selectively apply UV to only parts of the channel to immobilize proteins allowed the assay to be fabricated with no blocking steps, thus simplifying the fabrication process. The interaction between unactivated LAVAgel and introduced proteins was minimal, obviating the need to passivate non-patterned regions. Each patterning cycle was divided into three steps and could be repeated to create complex patterns within the microfluidic channel. The steps included loading, patterning and washing out of the unbound proteins. The process of fabricating a 5-band pattern using three distinct fluorescently labeled proteins in three patterning cycles is illustrated in FIG. 2 (panel A). During the first cycle, AF555 labeled OVA was first electrophoretically loaded into the channel and the photomask was placed on top of the chip and UV illumination was applied. The photomask blocked all UV from the chip except for two thin slits, which resulted in activation of two narrow regions of LAVAgel located beneath the unmasked region. AF555-labelled OVA was immobilized in the gel matrix at the exposure sites. Subsequent electrophoretic washout showed two fluorescent bands of captured protein. (FIG. 2 (panel A), Cycle 1). The process of load-pattern-wash was then repeated twice (with different masks) to pattern a single band of AF488-labelled OVA (FIG. 2 (panel A), Cycle 2), followed by two bands of AF488-labelled BSA (FIG. 2 (panel A), Cycle 3), for a total of five bands of three proteins. A composite image of the patterned bands is shown in FIG. 2 (panel A), Overlaid. An electropherogram of each of the three patterning cycles is shown in FIG. 2 (panel B). It can be seen that between Cycle 2 and Cycle 3 there was substantially no change in fluorescence signal in the regions between the patterned bands, which indicated that no residual fluorescent proteins were retained in the gel in the unexposed regions.

There was a depression in the fluorescence signals at the center of the patterned bands, which was the result of photobleaching of the fluorescent dyes under intense UV exposure and not due to higher immobilization efficiencies at the edges of the patterned bands. For example, based on manufacturer specifications, the intensity profile of light exiting the light guides was higher at the center and lower towards the edges. This indicated that any photobleaching effects would be more significant at the center than the edge. In addition, immunoprobing results suggested that there were more proteins immobilized at the center than the edges. As such, immunoprobing may be used for quantitation of local protein content, as compared to fluorescent labels on the immobilized proteins which may have photobleaching. This is consistent with the idea of higher UV exposure at the center of each illuminated band.

Capture of Antibody Using Patterned Bait Proteins

Figure 3:
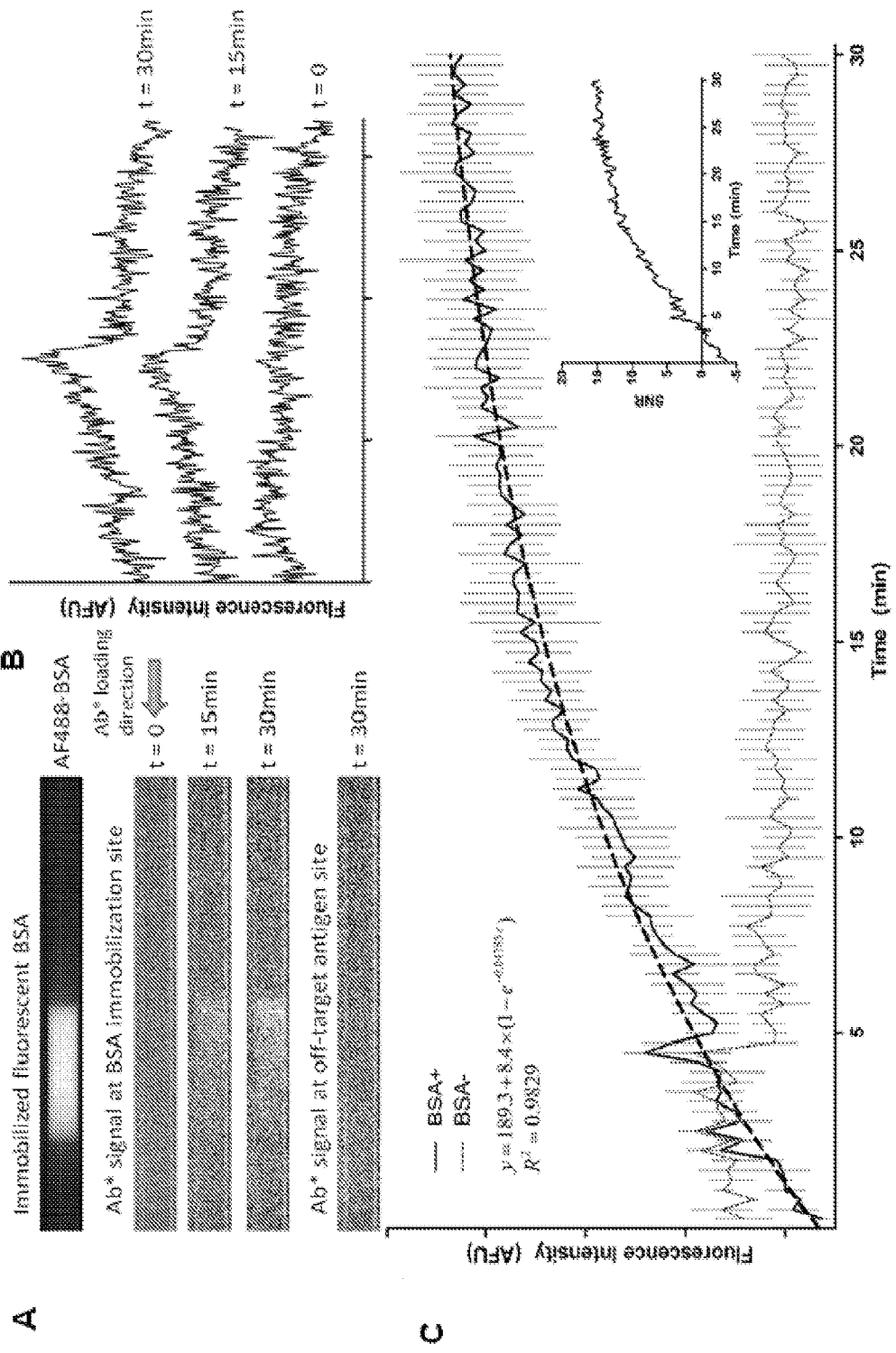
FIG. 3 (panel A) shows fluorescent images of a validation experiment using BSA and anti-BSA antibodies as an antibody-antigen pair, according to embodiments of the present disclosure.

Experiments were performed to demonstrate that the device was capable of capturing antibodies from a sample solution using the patterned protein capture members. To validate the ability of the platform as a diagnostic device, an initial characterization study was performed using BSA and anti-BSA antibodies as the antibody-antigen pair. The top image in FIG. 3 (panel A) shows a single photopatterned AF488-labeled BSA band. A dilute solution (~700 pM) of AF568-labeled anti-BSA antibody was electrophoretically loaded and the fluorescence signal at the location of the patterned protein band was monitored over time. The three images at the center of FIG. 3 (panel A) show fluorescence images taken at the beginning of antibody loading (t=0 min), fifteen minutes into the antibody loading, and at the end of the antibody loading phase at thirty minutes. The arrow indicates the direction of loading—right to left—in the current orientation. The bottom image in FIG. 3 (panel A) shows an image taken at the site of an immobilized off-target antigen at the end of the antibody loading phase (e.g., t=30 min). During the entire loading phase, the entire channel contained a uniform distribution of the antibody solution through the channel. However, as the concentration of antibody was loaded, the signal from the fluorescently labeled antibody was below that of the background noise. However, as the antibodies moved across the patterned protein band, they were captured through specific antibody/antigen interaction. This effectively increased the local concentration of the labeled antibody at the patterned protein band. As more antibodies were captured, a detectable signal emerged over time. In this case, since the antibody solution was loaded from right to left, the signal began to accumulate at the right side of the patterned band. This was visualized through electropherograms, as shown in FIG. 3 (panel B). The plots in FIG. 3 (panel B) show the corresponding electropherograms of the three center images shown in FIG. 3 (panel A). A noticeable peak was seen increasing as time progressed, indicating specific accumulation of antibody at the patterned BSA band.

The accumulation of antibody was monitored by taking a specific ROI (region of interest) at the patterned BSA band location and plotting the signal level over time during the antibody loading phase. FIG. 3 (panel C) shows a comparison between equivalent ROIs at the patterned BSA band and an off-target protein band as shown at the bottom of FIG. 3 (panel A). The solid line in FIG. 3 (panel C) shows the signal recorded at the BSA band and the dotted line shows the signal gathered at the off-target band. The vertical lines indicate the standard deviation of the measured signals at each time point with n=3 from three parallel channels within a single device. At the off-target site, the signal stayed constant over the entire thirty minute loading period, whereas the signal increased steadily over time at the BSA band. An exponential fit was applied to the data over the entire thirty minute range with an r-square value of 0.9829. This was consistent with antibody capture behavior at the leading edge. That is, as more antibodies became bound, the number of remaining available sites decreased, which slowed down the rate at which more antibodies were accumulated at the region. This was observed as a decrease in the slope of the curve over time. The significance of the captured antibody signal was evaluated in terms of the signal-to-noise ratio (SNR). The SNR was defined by the difference between the BSA+ signal and the BSA− signal divided by the averaged standard deviation of the BSA− signal. The inset in FIG. 3 (panel C) shows a graph of the SNR over the antibody loading period. After ten minutes, the SNR was greater than 5 and stayed above that value for the remainder of the antibody loading period.

Sandwich Assay in Microfluidic Barcode Format

Figure 4:
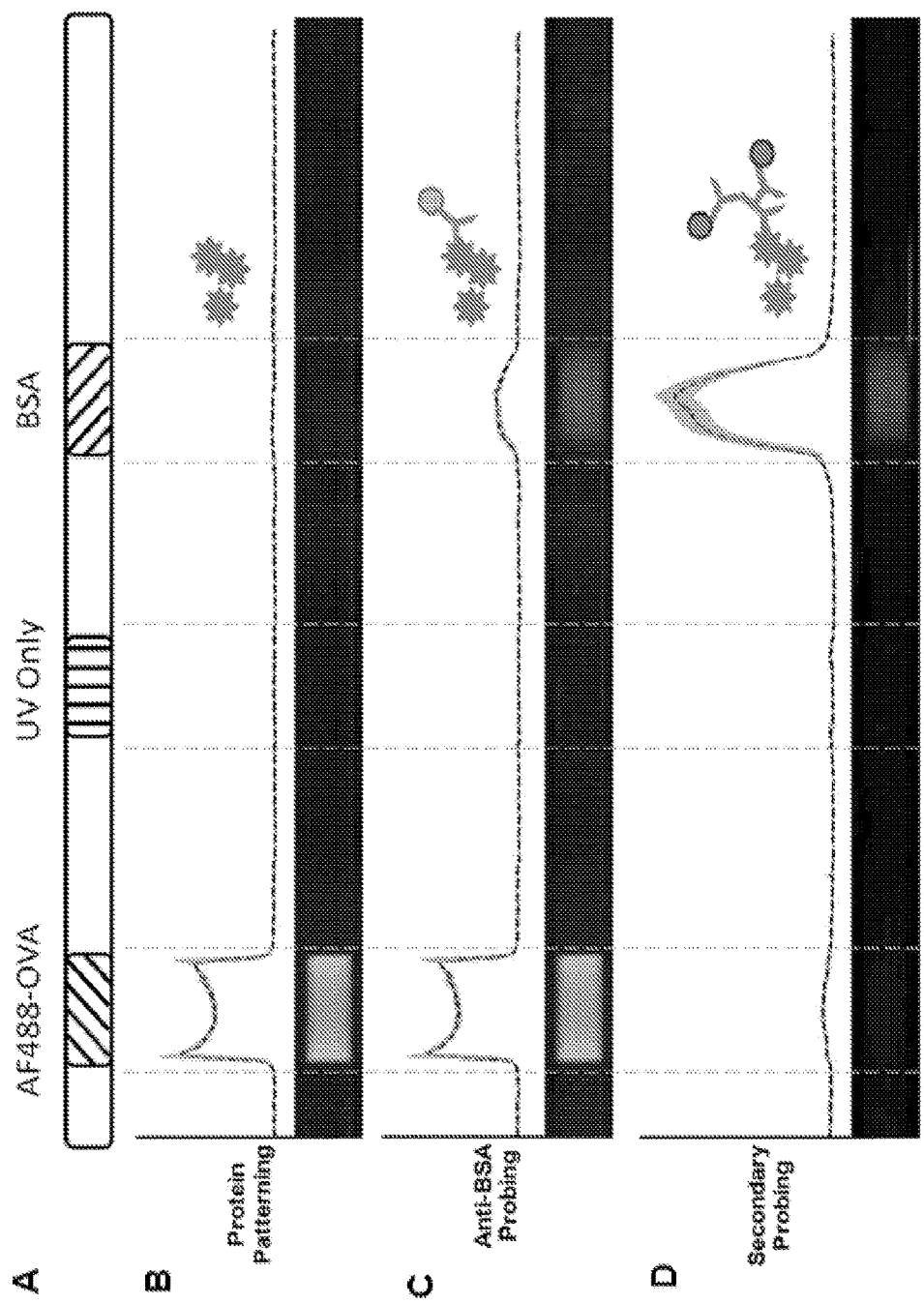
FIG. 4 (panels A-D) shows experiments indicating that a photopatterned protein band selectively captured antibody from loaded sample, according to embodiments of the present disclosure.

In order to evaluate the performance of a sandwich assay in the device disclosed herein, a 3-band test pattern was fabricated in a microfluidic channel. The three bands patterned were AF488-conjugated OVA, a band that was illuminated with UV only with no proteins immobilized, and a band of unlabelled BSA (see FIG. 4 (panel A)). The first two bands served as two negative controls. The OVA acted as an off-target antigen and the UV-activated band was a "blank" gel to ensure any signal present was not from nonspecific interactions between the antibodies and the gel. The bands were patterned in sequence from left to right. FIG. 4 (panel B) shows an image of a single microchannel after patterning of the three bands. Only a single band (AF488-OVA) was visible as the other two bands had no fluorescence. The electropherogram shows the mean signal value (dotted line) from three parallel channels and the shading around the dotted line indicates one standard deviation of the average signal. Photopatterning resulted in consistent protein immobilization between the three channels due to simultaneous UV illumination, as indicated by the minimal shading around the dotted line visible in the electropherogram. After patterning, 71.5 nM of sheep primary FITC-labeled anti-BSA antibody was electrophoretically introduced from right to left for 5 minutes followed by 10 minutes of electrophoretic washout. Fluorescence images were then taken of the microchannels to verify antibody capture. As can be seen in FIG. 4 (panel C), a specific fluorescent band was detected at the location where the BSA was photopatterned whereas locations with no BSA showed no signal. Additionally, there was no change in fluorescence signal at the AF488-OVA band, indicating no significant crossreactivity at the off-target antigen location. The electropherogram showed the consistency between the three technical triplicates with minimal visible shaded area (standard deviation), which indicated a tight distribution. To complete the sandwich assay, 71.5 nM of AF568-labelled goat-anti-sheep secondary antibody was loaded into the device from right to left for ten minutes followed by ten minutes of washout. The immunoblotting result is shown in FIG. 4 (panel D). The secondary antibody produced a significant increase in signal compared to the baseline at the BSA band location. Additionally, the SNR of the integrated fluorescence at the BSA band compared to the UV-only band increased from ~25 for the primary probing to >100 with the secondary probe. Over the same sized ROI, the SNR for secondary signal at the AF488-OVA (off-target antigen) was only ~6.8. The results indicated that the device finds use in specifically capturing and identifying antibodies in samples loaded into the device.

HCV Diagnostic with Human Serum Sample

Figure 5:
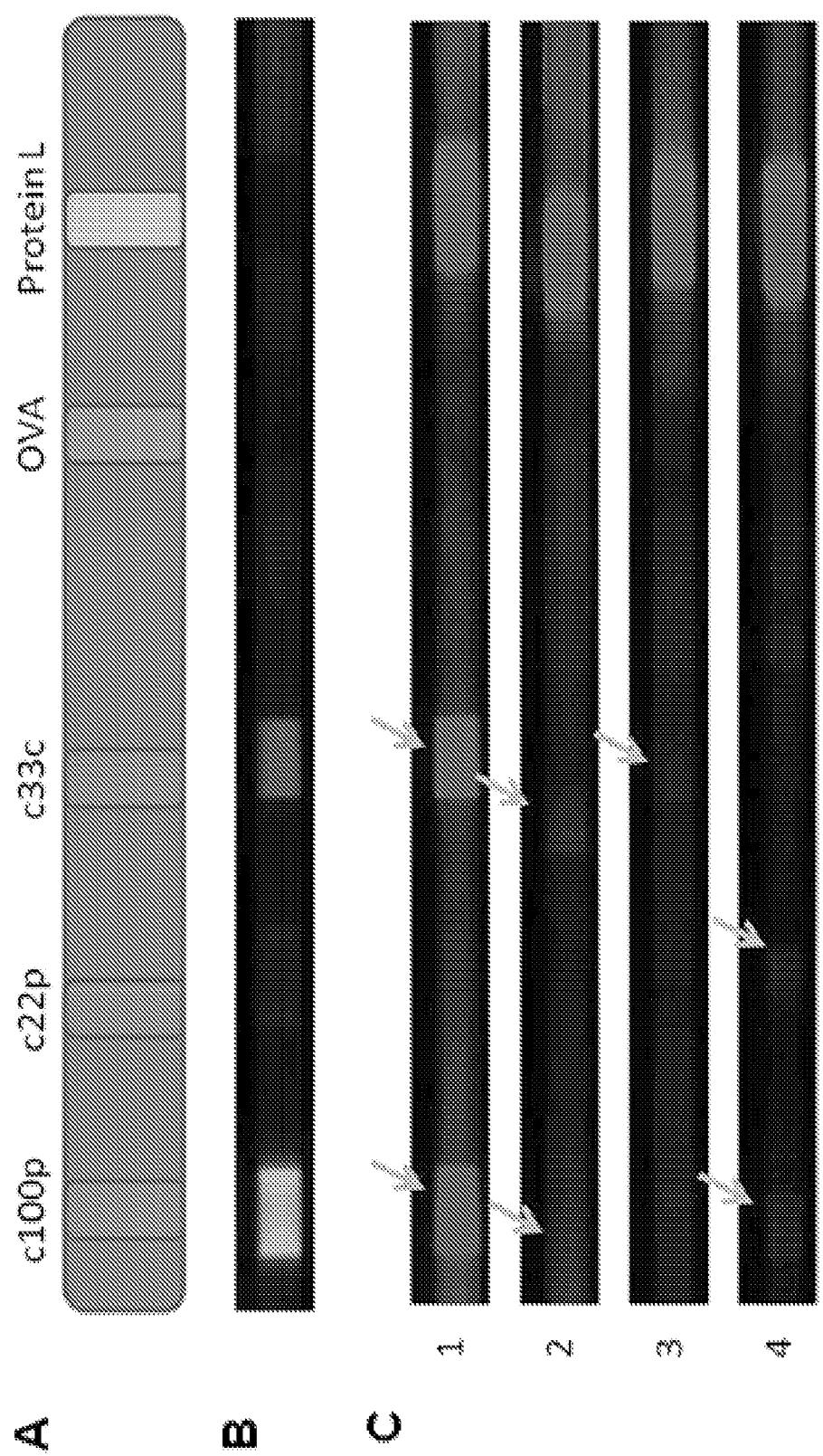
FIG. 5 (panel A) shows a schematic of a HCV diagnostic band layout in a device configured to detect HCV antibodies in a human serum sample, according to embodiments of the present disclosure.

After verifying that the device can be used to capture and identify antibodies, experiments were performed to examine human sera with patterned HCV antigens. For a HCV diagnostic assay, a five band pattern was used including three AF488-labeled HCV antigens, one negative control (OVA), and one positive control band patterned with protein L to verify successful loading of the serum. FIG. 5 (panel A) shows a schematic of the HCV diagnostic band layout. The three HCV antigens used were c100p (peptide from NS4—membrane binding protein), c22p (peptide from core protein) and c33c (viral protein NS3—virus protease). The bands were patterned in sequence from left to right. FIG. 5 (panel B) shows a fluorescence image taken after patterning of all five bands. The three HCV antigens were detected on the left side of the microchannel, while the negative and positive controls were unlabelled and were not detected.

Human serum samples are diluted 1:40 into 1× Tris-Glycine buffer and electrophoretically loaded into the patterned microchannels for fifteen minutes followed by twenty minutes of washout with 1×TG buffer. The volume of human serum consumed per triplicate assay was approximately 150 nL. After washout, immunoblotting was performed by introducing 71.5 nM of AF568-labelled anti-human secondary antibody for ten minutes followed by ten minutes of washout.

The microfluidic chip format facilitated the performance of four simultaneous assays per chip with technical triplicates for each assay. FIG. 5 (panel C) shows results from four simultaneous assays performed on four different human serum samples. One of the four samples was from a HCV− individual, and the other three samples were from known HCV+ patients. The positive control (protein L) showed a signal for all four samples indicating that sera was successfully loaded in all four devices. The negative control band (OVA) showed no signal in each of the four cases. For the HCV antigen bands, the HCV− serum (Serum #4) showed no significant signal, which indicated no reactivity towards the HCV antigens. The HCV+ serums showed a gradient of probed results. Serum #1 showed high reactivity against c100p and c33c, with no reactivity against c22p. Serum #2 showed low response against c100p and c33c, with no reactivity against c22p. Serum #3 showed low response to c100p and c22c, and a relatively higher response against c33c. HCV+ serums may show variable response to HCV antigens, as studies using recombinant immunoblot assay (RIBA) diagnostic devices have shown that not all HCV+ patients show positive response to antibody-based diagnostic tests.

SUMMARY AND CONCLUSION

A functionalized polyacrylamide gel matrix (LAVAgel) was used for photopatterning complex patterns in microfluidic devices. Highly reproducible three-dimensional immobilized protein patterns were produced rapidly. With no grafting, pre-patterning or blocking steps required, patterning of specific proteins was achieved in a single step. The functionalized polyacrylamide gel matrix containing microfluidic device was used to create a multiplexed assay platform that detected specific antibodies from a sample using patterned immobilized antigen proteins. The device was used as a multiplexed microfluidic HCV diagnostic tool that was capable of detecting human anti-HCV antibodies from dilute human patient sera. In addition to fabrication of diagnostic platforms, photopatterning using the functionalized polyacrylamide gel matrix finds use in other complex geometries as the fabrication method can be used for multiple rounds of patterning. The devices, system and methods disclosed herein find use in applications such as assays for substrate-enzyme or signal-receptor interactions. The ability to produce arbitrary patterns also facilitates the creation of more complex multi-stage assays that would otherwise be prohibitive due to long and complex multi-step fabrication protocols.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A microfluidic device comprising:
a contiguous polymeric medium disposed in at least a portion of a flow path of the microfluidic device comprising:
   (a) a first analyte detection domain comprising a first covalently bound capture member that specifically binds to a first analyte, wherein the first covalently bound capture member is covalently bound to the polymeric medium through a linker group comprising a benzophenone functional group;
   (b) a second analyte detection domain comprising a second covalently bound capture member that specifically binds to a second analyte, wherein the second covalently bound capture member is covalently bound to the polymeric medium through a linker group comprising a benzophenone functional group; and
   (c) spacer domain comprising the contiguous polymeric medium and not including a significant amount of the capture members, wherein the spacer domain is a distinct domain disposed between the first and second analyte detection domains, and the spacer domain is in fluid communication with the first and second analyte detection domains.

2. The microfluidic device of claim 1, wherein the first and second covalently bound capture members are different.

3. The microfluidic device of claim 1, wherein the first and second covalently bound capture members are the same.

4. The microfluidic device of claim 1, wherein the polymeric medium comprises a polyacrylamide gel.

5. The microfluidic device of claim 1, wherein the linker group comprises N-(3-[(4-benzoylphenyl)formamido]propyl) methacrylamide or 3-benzoyl-N-[3-(2-methyl-acryloylamino)-propyl]-benzamide.

6. The microfluidic device of claim 1, wherein the first capture member comprises an antigen.

7. The microfluidic device of claim 1, wherein the second capture member comprises an antigen.

8. The microfluidic device of claim 1, wherein the microfluidic device comprises:
two or more contiguous polymeric media disposed in at least a portion of a flow path of the microfluidic device, each of which comprises:
   (a) a first analyte detection domain comprising a first covalently bound capture member that specifically binds to a first analyte, wherein the first covalently bound capture member is covalently bound to the polymeric medium through a linker group comprising a benzophenone functional group;
   (b) a second analyte detection domain comprising a second covalently bound capture member that specifically binds to a second analyte, wherein the second covalently bound capture member is covalently bound to the polymeric medium through a linker group comprising a benzophenone functional group; and
   (c) a spacer domain comprising the contiguous polymeric medium and not including a significant amount of the capture members, wherein the spacer domain is a distinct domain disposed between the first and second analyte detection domains, and the spacer domain is in fluid communication with the first and second analyte detection domains.

9. A method of determining whether an analyte is present in a sample, the method comprising:
   (a) introducing a sample into a microfluidic device comprising a contiguous polymeric medium media disposed in at least a portion of a flow path of the microfluidic device, wherein the polymeric medium comprises:
      (i) a first analyte detection domain comprising a first covalently bound capture member that specifically binds to a first analyte, wherein the first covalently bound capture member is covalently bound to the polymeric medium through a linker group comprising a benzophenone functional group;
      (ii) a second analyte detection domain comprising a second covalently bound capture member that specifically binds to a second analyte, wherein the second covalently bound capture member is covalently bound to the polymeric medium through a linker group comprising a benzophenone functional group; and
      (iii) a spacer domain comprising the contiguous polymeric medium and not including a significant amount of the capture members, wherein the spacer domain is a distinct domain disposed between the first and second analyte detection domains, and the spacer domain is in fluid communication with the first and second analyte detection domains;
   (b) applying a directional electric field to the polymeric medium in a manner sufficient to move components in the sample through the polymeric medium; and
   (c) obtaining a signal from one or more of the first and second analyte detection domains to determine whether the analyte is present in the sample.

10. The method of claim 9, wherein the first capture member comprises a first antigen and the first analyte comprises a first specific binding member that specifically binds to the first antigen.

11. The method of claim 9, wherein the second capture member comprises a second antigen and the second analyte comprises a second specific binding member that specifically binds to the second antigen.

12. The method of claim 10, wherein the first specific binding member comprises a fluorescent label.

13. The method of claim 11, wherein the second specific binding member comprises a fluorescent label.

14. The method of claim 9, further comprising introducing a label into the microfluidic device after introducing the sample into the microfluidic device.

15. The method of claim 14, wherein the label comprises a secondary specific binding member that specifically binds to the first analyte.

16. The method of claim 14, wherein the label comprises a secondary specific binding member that specifically binds to the second analyte.

17. The method of claim 14, wherein the label comprises a fluorescent moiety.

18. The method of claim 9, wherein the sample comprises blood or a blood product.

19. A system for determining whether an analyte is present in a sample, the system comprising:
    (a) a microfluidic device according to claim 1; and
    (b) a detector.

20. The system according to claim 19, further comprising one or more microfluidic components configured to direct a fluid through the microfluidic device.

21. A kit comprising:
    (a) a microfluidic device according to claim 1;
    (b) a packaging configured to contain the microfluidic device.

22. A method of producing a microfluidic assay device, the method comprising:
    producing a contiguous polymeric medium disposed in at least a portion of a flow path of the microfluidic device and comprising benzophenone functional groups that covalently bond to a capture member upon application of an applied stimulus;
    introducing into the polymeric medium a first capture member that specifically binds to a first analyte;
    exposing a first region of the polymeric medium to the applied stimulus to produce a first analyte detection domain that comprises the first capture member covalently bound to the polymeric medium through a linker group comprising a benzophenone functional group;
    introducing into the polymeric medium a second capture member that specifically binds to a second analyte; and
    exposing a second region of the polymeric medium to the applied stimulus to produce a second analyte detection domain that comprises the second capture member covalently bound to the polymeric medium through a linker group comprising a benzophenone functional group,
    to produce the microfluidic assay device,
        wherein the contiguous polymeric medium comprises a distinct spacer domain which does not comprise a significant amount of the capture members and which is disposed between the first and second analyte detection domains, and wherein the spacer domain is in fluid communication with the first and second analyte detection domains.

23. The microfluidic device of claim 1, wherein the spacer domain is adjacent to the first and second analyte domains.

* * * * *